US006414133B1

(12) United States Patent
Dietz-Band et al.

(10) Patent No.: US 6,414,133 B1
(45) Date of Patent: Jul. 2, 2002

(54) MULTIPLE FUSION PROBES

(75) Inventors: Jeanne Dietz-Band, Keedysville; Wang-Ting Hsieh, Bethesda; John F. Connaughton, Laytonsville, all of MD (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/170,630

(22) Filed: Oct. 13, 1998

(51) Int. Cl.$^7$ .......................... C07H 21/04; C12Q 1/68; C12P 19/34
(52) U.S. Cl. ................ 536/24.3; 536/24.31; 536/24.32; 536/24.33; 536/23.1; 435/6; 435/91.1
(58) Field of Search ............................. 536/24.3, 25.3, 536/23.1, 24.31, 24.33, 24.32; 435/6, 91.1, 2, 91.2, 810

(56) References Cited

U.S. PATENT DOCUMENTS

| 4,999,290 A |   | 3/1991  | Lee ................................ 435/6 |
| 5,487,970 A | * | 1/1996  | Rowley et al. ................ 435/6 |
| 5,538,869 A |   | 7/1996  | Sicilliano et al. .......... 435/91.2 |
| 5,567,586 A | * | 10/1996 | Croce ............................ 435/6 |

OTHER PUBLICATIONS

TKachuk et al. Detection of BCR–ABL Fusion in Chronic Myelogeneous Leukemia by in situ Hybridization. Science. vol. 250, pp. 559–562, Nov. 1990.*
Fischer et al. Design and Validation of DNA Probe Sets for a Comprehensive Interphase Cytogenetic Analysis of Acute Myeloid Leukemia. Blood. vol. 88, pp. 3962–3971, Nov. 1996.*
Dewald et al, Blood, 91(9); pp. 3357–3365 (May 1, 1998).
Paskulin et al, Genes, Chromosomes & Cancer 21: 144–151 (1998).

Oncor 1992–1993 Product Catalog, p. 11 Oncor, Inc. 209 Perry Pky. Gaithersburg, MD.
1996/1997 Catalog, Vysis, Inc. 3100 Woodcreek Drive, Downers Grove, IL pp. 25 and 30.
TKachuk et al. Detection of BCR–ABL Fusion in Chronic Myelogeneous Leukemia by in situ Hybridization. Science. vol. 250, pp. 559–562, Oct. 1990.*
Dewald et al. Highly sensitive fluorescence in situ hybridization method to detect double BCR/ABL fusion and monitor response to therapy in chronic myeloid leukemia. Blood. vol. 91, No. 9, pp. 3357–3365, May 1998.*
Paskulin et al. Pre–Clinical Evaluation of Probes to detect t(8;21) AML minimal residual disease by fluorescence in situ hybridization. Genes, Chromosome and Cancer vol. 21, pp. 144–151, Feb. 1998.*

* cited by examiner

Primary Examiner—W. Gary Jones
Assistant Examiner—Cynthia Wilder
(74) Attorney, Agent, or Firm—Huw R. Jones; John E. Tarcza; Ann S. Hobbs

(57) ABSTRACT

The invention is directed to a DNA probe set, the probe set comprising a first probe set and a second probe set, the first probe set being sufficient in length and substantially complementary to an entire breakpoint region of a first DNA and nucleotides breakpoint region but less than an entire chromosome such that the first probe set will hybridize to both sides of the breakpoint region regardless of whether the first DNA has been broken in the breakpoint region and either end fused to another DNA, and the second probe set being sufficient in length and substantially complementary to an entire breakpoint region of a second DNA and nucleotides on both sides of the breakpoint region but less than an entire chromosome such that the second probe set will hybridize to both sides of the breakpoint region regardless of whether the second DNA has been broken in the breakpoint region and either end fused to another DNA. Diagnostic kits utilizing the probe sets of the invention are also claimed.

19 Claims, 10 Drawing Sheets

(1 of 10 Drawing Sheet(s) Filed in Color)

SCORING KEY:
R = RED SIGNAL = BCR
G = GREEN SIGNAL = ABL1
F = YELLOW SIGNAL BCR/ABL1 FUSION

SCORING KEY:
R = RED SIGNAL = BCR
G = GREEN SIGNAL = ABL1
F = YELLOW SIGNAL BCR/ABL1 FUSION

SCORING KEY:
R = RED SIGNAL = BCR
G = GREEN SIGNAL = ABL1
F = YELLOW SIGNAL BCR/ABL1 FUSION

SCORING KEY:
R = RED SIGNAL = BCR
G = GREEN SIGNAL = ABL1
F = YELLOW SIGNAL BCR/ABL1 FUSION

TABLE 1: BCR SUMMARY

MAPPING OF BCR CLONES
BCR REGION CONTAINS 152,141 BP PUBLISHED SEQUENCE

| NAME OF CLONE | CLONE TYPE | PRIMER PAIRS | | | | | | | | CLONE SIZE (Kb) |
| --- | --- | --- | --- | --- | --- | --- | --- | --- | --- | --- |
| | | BCR26/27 | BCR13/14 | BCRA/B | BCRC/D | BCRE/F | BCR11/12 | BCR17/18 | | |
| OCB 1004 | PAC | | | + | + | + | | | | 214 |
| OCB 1005 | PAC | | | | | | | | | 105 |
| OCB 1001 | PAC | + | + | | | | | | | 154 |
| OCB 1002 | PAC | + | + | + | | | | | | 127 |
| OCB 1003 | PAC | + | − | | | | | | | 147 |

+ : THE CLONE CONTAINS THE SEQUENCE AMPLIFIED BY THIS PRIMER SET.
− : THE CLONE DOES NOT CONTAIN THE SEQUENCE AMPLIFIED BY THIS PRIMER SET.

FIG. 7

TABLE 2: ABL SUMMARY

MAPPING OF ABL CLONES

3 SEQUENCES ARE AVAILABLE:

HSABLGR1, 35,692 BP, 5' ABL, EXON1B(29132-29267)/INTRON 1B(29268-35692)
HSABLGR2, 59,012 BP, PARTIAL INTRON 1B
HSABLGR3, 84,539 BP, INTRON 1B(1-37824)/EXON1A TO EXON10 AND POLYA

| NAME OF CLONE | CLONE TYPE | PRIMER PAIRS | | | | | | | | CLONE SIZE (Kb) |
|---|---|---|---|---|---|---|---|---|---|---|
| | | ABL5/6 | ABL3/4 | ABLa/b | ABLe/f | ABL9/10 | ABLc/d | ABL7/8 | ABL19/20 | |
| OC3002 | P1 | − | − | + | + | + | − | | | 88 |
| OCA1003 | BAC | + | + | + | − | | | | | 101 |
| OCA1001 | PAC | + | − | − | − | | | | | 181 |
| OCA1004 | YAC | | | | | + | + | + | − | 250 |
| OCA1005 | PAC | | | | | | − | + | + | 186 |
| OCA1006 | PAC | | | | | | − | + | + | 153 |
| OCA1007 | PAC | | | | | | − | − | + | 138 |

+ : THE CLONE CONTAINS THE SEQUENCE AMPLIFIED BY THIS PRIMER SET.
− : THE CLONE DOES NOT CONTAIN THE SEQUENCE AMPLIFIED BY THIS PRIMER SET.

FIG. 8

TABLE 3

| | | 500 NUCLEI | | | 6,000 NUCLEI | | | | HYPERMETAPHASE BONE MARROW |
|---|---|---|---|---|---|---|---|---|---|
| | | BONE MARROW | | PERIPHERAL BLOOD | | BONE MARROW | | PERIPHERAL BLOOD | % ABN (PH POSITIVE/ |
| | | | ABN | | ABN | | ABN | | ABN |
| PT | SPEC | %ABN | NUCLEI | %ABN | NUCLEI | %ABN | NUCLEI | %ABN | NUCLEI | METAPHASES ANALYZED |
| 4 | 3 | 0.6% | 3 | 0.2% | 1 | 0.22% | 13 | 0.10% | 6 | 0.0%(0/27) |
| 4 | 4 | 0.4% | 2 | 0.2% | 1 | 0.23% | 14 | 0.08% | 5 | 0.0%(0/15) |
| 4 | 5 | 0.0% | 0 | 0.0% | 0 | NA | NA | 0.13% | 8 | 0.0%(1/169) |
| 5 | 3 | 0.6% | 3 | 1.0% | 5 | 1.30% | 78 | 0.95% | 57 | 0.0%(0/136) |
| 5 | 4 | 0.0% | 0 | 0.2% | 1 | 0.05% | 3 | 0.12% | 7 | 0.0%(0/126) |
| NORMAL CUTOFF | | >0.8% | >4 | >0.8% | >4 | >0.079% | >4 | >0.079% | >4 | |

FIG. 9

TABLE 4

| SAMPLE | PTS | MEAN PROPORTIONS (+SE) ORIGINAL SCALE | | ADJUSTED MEAN DELTA (+SE) (TRANSFORMED SCALE) |
|---|---|---|---|---|
| | | BONE MARROW | BLOOD | |
| DX | 10 | 0.91 (±0.05) | 0.75 (±0.08) | 0.165 (±0.047) |
| 4 MOS | 10 | 0.56 (±0.10) | 0.41 (±0.09) | 0.177 (±0.042) |
| 8 MOS | 10 | 0.49 (±0.13) | 0.39 (±0.11) | 0.150 (±0.042) |
| 12 MOS | 6 | 0.32 (±0.13) | 0.20 (±0.08) | 0.181 (±0.054) |

FIG. 10

MULTIPLE FUSION PROBES

FIELD OF THE INVENTION

The invention relates to improved polynucleotide probe configurations for detecting structural abnormalities that result from chromosome breakage and rearrangement, particularly as used in the detection of several types of genetic disorders related to cancer and other diseases. The invention further relates to an improved method of detecting translocations using probe sets which span each breakpoint region associated with a translocation and the regions on both sides beyond the 3' and 5' ends of each breakpoint region.

BACKGROUND OF THE INVENTION

A number of inherited genetic diseases and types of cancer have been linked to chromosomal translocation events which result in the fusion of two genes which do not occur together in the normal genome. Certain conditions involve translocations which frequently occur at the same or very near location. The chromosome regions where frequent breaks occur are called breakpoint regions.

One of the best known examples of a clinically important translocation is the Philadelphia Chromosome which results from a break in the ABL1 gene on distal chromosome 9q and the BCR gene on proximal chromosome 22q {t(9;22)} (FIG. 1). The breakpoints within the ABL1 gene may occur throughout a region spanning more than 175 kb upstream from exon II while the breaks in chromosome 22 are clustered into two areas of the BCR gene, termed the major breakpoint cluster region (m-bcr) and the minor breakpoint cluster region (M-bcr) (Kurzrock et al, *New England Journal of Medicine*, 319:990 (1988)). The Philadelphia Chromosome occurs in most cases of Chronic Myelogenous Leukemia (CML) and some cases of Acute Lymphocytic Leukemia (ALL). Other important translocations include, but are not limited to, t(8;21) in Acute Myelogenous Leukemia, t(8:14) in Burkett's Lymphoma and pre-B-cell Acute Lymphoblastic Leukemia, t(1:14), t(7:9), t(7:19), t(11:14), t(10:14) and t(7:9) in T-acute Lymphoblastic Leukemia, t(15;17) in Acute Myelogenous Leukemia (AML) and t(15:17) Acute Promyelocytic Leukemia (PML). Solid tumors include, t(9;22) in Ewing's Sarcoma, t(15:16), and hereditary diseases associated with translocations include a number of mental retardation associated syndromes. It is likely that other conditions are caused by subcriptic translocations or other structural aberrations which are yet to be determined and are too small to be noticed by standard cytogenetics.

Multiple genetic testing methods have been developed for use in diagnosis, monitoring of minimal residual disease and/or response to therapy during clinical practice. However, no single technique has been developed that can accurately detect and quantify disease at diagnosis and throughout treatment. Conventional quantitative cytogenetics and G-banding analysis is cumbersome and can only be applied to cycling cells (Lion, Leukemia 10: 896 (1996)). In practice, the sensitivity of conventional cytogenetics is dependent upon the number of good metaphase cells which can be evaluated. In the example of cancers caused by neoplastic cells in the bone marrow, obtaining large numbers of good metaphase cells from bone marrows of patients is difficult.

More recently, the assay technique in situ hybridization (ISH), particularly fluorescent in situ hybridization (FISH) (Pinkel et al, *Proc. Natl. Acad. Sci., U.S.A.* 83:2934–2938 (1986)) has been of assistance in detecting translocations. FISH allows the analysis of individual metaphase or interphase cells, thereby eliminating the need to obtain and assay cycling cells. It is therefore possible to use nondividing tissue, including bone marrow and peripheral blood cells in a diagnostic or prognostic analysis.

In the field of detecting the Philadelphia Chromosome, a commonly used method for detection of ABL1/BCR fusion utilizes differently labeled probes for BCR and ABL1, and detects a single ABL1/BCR fusion (or closely linked) signal in cells with a Ph chromosome. (This method is referred to for convenience as S-FISH.) An example of this technique is Tkachuk et al, *Science* 250: p. 559–562 (1990) where one fluorescently labeled probe hybridized to part of the ABL1 gene and a second fluorescently labeled probe hybridized to part of the BCR gene.

The probes in commercial single FISH test kits do not span the entire length of each translocation breakpoint but rather are designed to bind to one portion of each gene, i.e. sometimes overlapping or adjacent to a breakpoint region, sometimes many kilobases away and sometimes both (See FIG. 1 of Tkachuk et al for example). Normal chromosomes 9 and 22 each bind one probe, which is specific to that chromosome. The Philadelphia Chromosome, both probes hybridize at the fusion site bringing both labels in close proximity so as to usually form a color shift or fusion near proximity/signal. Because the exact breakpoint may vary, the two probe labels may not come sufficiently close to form a fusion label. Likewise for probes useable to detect the t(8;21) translocation in Acute Myelogenous Leukemia (AML).

Using the probe configuration above, the following detection method for the Philadelphia Chromosome using FISH has been used: the ABL1 gene probe is labeled using a probe containing one hapten or fluorophore (for example, FITC) and the BCR gene probe is labeled using a probe containing another hapten or fluorophore (for example Rhodamine). After hybridization and detection, a normal chromosome 9 shows the green signal and a normal chromosome 22 shows a red signal. A normal cell would therefore exhibit two red signals and two green signals. A cell containing a Philadelphia chromosome has one red and one green signal for the unaffected homologues of chromosomes 9 and 22 and one white, yellow or closely linked pair of signals that results from the close proximity of the labeled probes hybridized to the translocated BCR and ABL1 genes, the so-called fusion signal.

However, the probes used heretofore in this method have not been constructed so as to specifically bind and detect the second fusion site for the reciprocal translocation event. Thus, the S-FISH method detects only one of the abnormal chromosomes resulting from the translocation event, the Philadelphia chromosome.

In another method using labelled probes to detect ALL gene rearrangements in solid tumors, a probe set was designed so that the two probes lie adjacent to each other on the normal chromosome, but split apart and move to the two different abnormal chromosomes if the translocation has occurred (Croce, U.S. Pat. No. 5,567,586, hereby incorporated by reference). In this method the probes are designed to be complementary to sequences in the translocation region on one chromosome. In this method, the fluorescent probes produce a single spot on the normal chromosome, but appear as two distinct spots when translocation has occurred.

The same format has been used for other assays for detecting other translocations such as t(8:21) in Acute Myeloid Leukemia (AML). For example, Le Beau, Blood 81: 1979–1983 (1993), and Sacchi et al, Cancer Genetics and Cytogenetics 79: 97–103 (1995) and Fischer et al, Blood 88: 3962–3971 (1996).

SUMMARY OF THE INVENTION

It is an object of the invention to provide methods with increased sensitivity and accuracy for detecting chromosome translocations and other structural rearrangements which result in more than one abnormal fusion site in the genome.

It is a further object of the invention to provide probes and probe sets which are useful in detecting reciprocal genetic translocations according to the methods of the invention.

It is another object of the present invention to detect cancer, inherited disease, susceptibility to inherited disease or a carrier of a fused gene for an inherited disease wherein the condition results from a chromosomal translocation in one or more cells. This is particularly beneficial when the diagnosis, prognosis, monitoring for residual disease and response to therapy in cancer or other disease is dependant upon the quantity of abnormal cells as an indicia of the disease state and/or response to treatment.

It is also an object of the invention to provide a means of constructing such probes and probe sets, which will detect reciprocal fusions resulting from chromosomal translocations and will accordingly be useful in diagnosis, prognosis, monitoring of residual disease and response to therapy when reciprocal chromosome translocations are present.

It is still another object of the present invention to provide diagnostic test kits which can be used by any cytogenetist or other trained individual to detect multiple fusion events which result from structural rearrangement of the genome.

Probes and probe sets of the present invention have the characteristic of encompassing the entire breakpoint region and a region on each side of the breakpoint region on each chromosome for the reciprocal translocation event of interest and are capable of detecting such translocations with much greater sensitivity than the probes and probe sets which were previously known.

A particularly preferred probe set and method is used for detecting the Philadelphia chromosome and its corresponding derivative chromosome as companion indicators of CML and some other cancers such as ALL. One functional probe is designated P5161-DC, described hereinbelow. Another example is for detecting the AML1/ETO gene fusion in AML.

The use of specifically designed probe sets by the method of the present invention has allowed the clinician to assess physical information regarding all fusion events associated with a defined structural rearrangement in a cell. For example, using the standard detection method of fluorescence in situ hybridization (FISH) it has been demonstrated that these probe sets provide the following advantages over traditional testing methodologies for detecting the same translocation.

1. Unlike traditional single fusion probe sets, probe sets which detect multiple, derivatives of a structural rearrangement have the ability to detect much lower copy numbers of abnormal cells thereby providing greater improved diagnostics using FISH assays
2. The ability of the probe sets to derive necessary information from cells in interphase, Thereby rivaling the sensitivity of metaphase cells in conventional cytogenetics.
3. Specifically, increased sensitivity has been demonstrated with multiple fusion probes used in interphase FISH analysis which is at least as sensitive as Q-cytogenetics (the previous gold standard) for monitoring bone marrow or peripheral blood cell populations for minimal residual disease and response to therapy.
4. Greater sensitivity allows the use of peripheral blood instead of invasive and painful bone marrow samples from patients for routine testing, to monitor for minimal residual disease and response to therapy.
5. By detecting high and low copy numbers of gene fusions, the present invention can be used for diagnosis and monitoring throughout the course of the disease thereby avoiding traditional multiple assay-type testing methodologies.
6. Simplified sample requirements and testing provides further benefits in cost and patient well being.

BRIEF DESCRIPTION OF THE DRAWINGS

The file of this patent contains at least one drawing executed in color. Copies of this patent with color drawing will be provided by the Patent and Trademark Office upon request and payment of the necessary fee.

FIG. 7. BCR map and summary of probe listed as Table 1.

FIG. 8. ABL1 map and summary of probe listed as Table 2.

FIG. 9. Data and comparison of different techniques for assaying for the Philadelphia chromosome, listed as Table 3.

FIG. 10. Data comparing bone marrow and blood samples for monitoring the disease state and response to therapy, listed as Table 4.

DETAILED DESCRIPTION OF THE INVENTION

Figure 1:
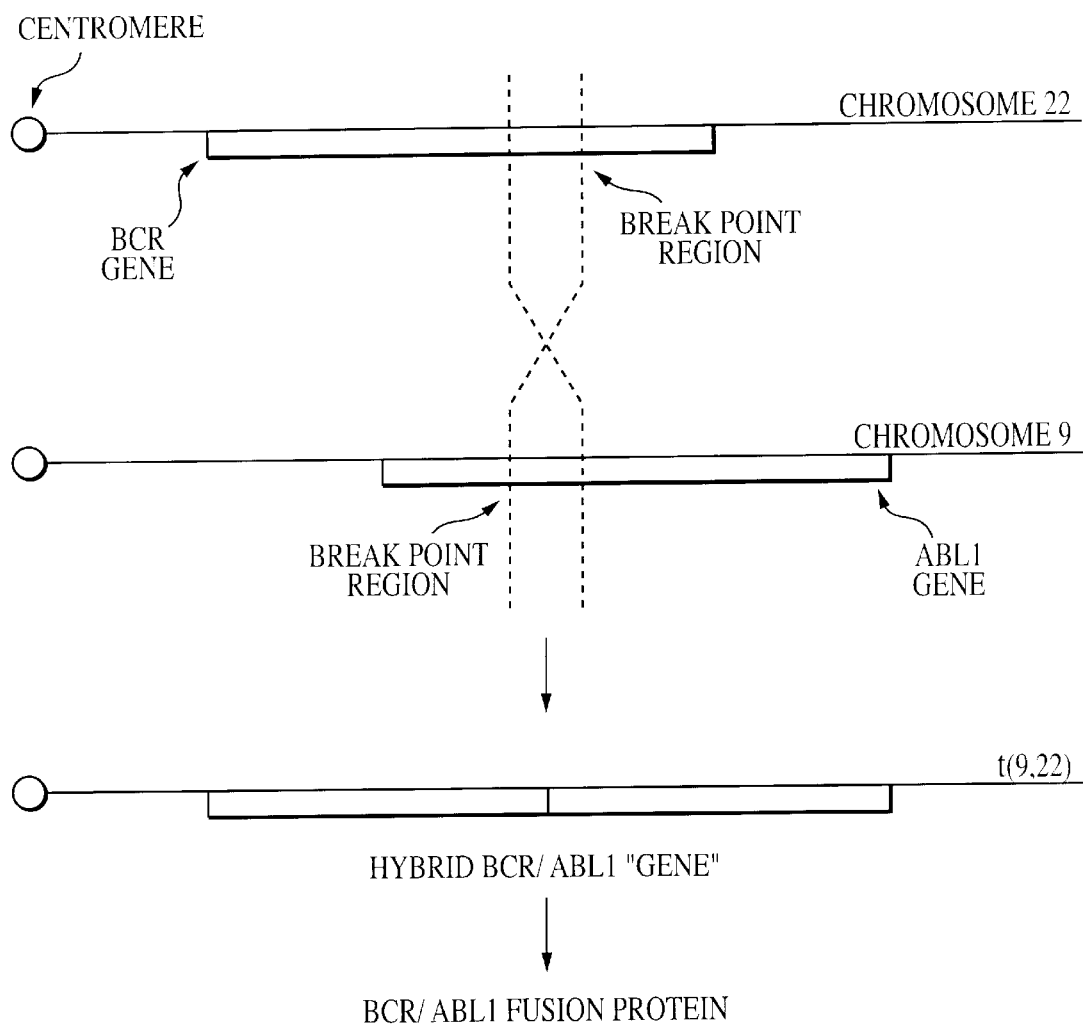
FIG. 1 shows a schematic drawing of a BCR/ABL1 translocation and probes constructed according to the invention.
Figure 2A:
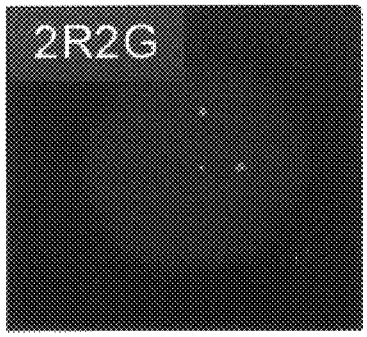
FIG. 2A shows the appearance of a normal cell after testing with probe P5161-DC using the methods of the invention. The two red signals designate the BCR genes on chromosome 22 and the two green signals designate the ABL1 genes on chromosome 9.
Figure 2B:
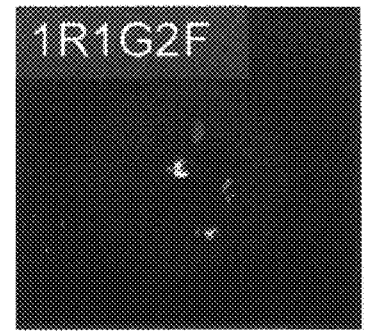
FIG. 2B shows the appearance of a cell containing a BCR/ABL1 translocation after testing with probe P5161-DC using the methods of the invention. One red, one green and two fused signals denoting both of the reciprocal translocation events are present.
Figure 2C:
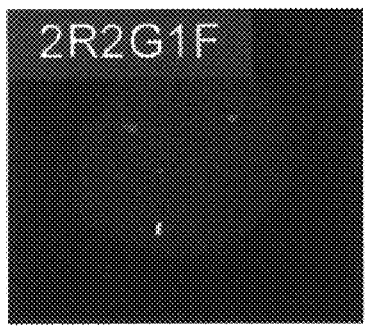
FIG. 2C also shows the appearance of a cell containing a BCR/ABL1 translocation after testing with probe P5161-DC using the methods of the invention. Two red, two green and one fused signals are present in this example. While two fusion signals are usually detected, because of the physical configuration of the gene and the relaxation of the heterochromatin in interphase, a red and a green signal may appear to be closely linked but not quite overlapping. Note the two signals at the lower end of the field which are not quite fused. This configuration is believed to represent the fused portion of a translocation event.
Figure 2D:
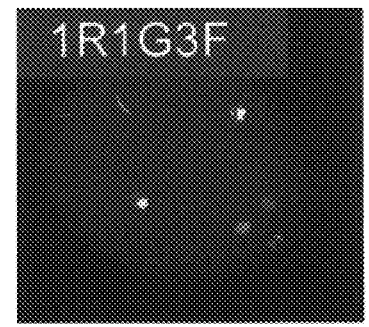
FIG. 2D shows the appearance of a cell containing a BCR/ABL1 translocation after testing with probe P5161-DC using the methods of the invention. One red, one green and three fused signals are present. This cell contains an additional Philadelphia chromosome.

The present invention is an assay and reagents therefore which may be packaged into a simple test kit. The reagent comprises two probes, the first complementary to and encompassing the entire breakpoint region on a first chromosome as well as both upstream and downstream regions from the breakpoint region. As such, the first probe will hybridize to a normal first chromosome as well as both fragments of the first chromosome which have undergone a translocation or break and may be rearranged elsewhere. The second probe is the same as the first except for spanning the entire breakpoint region, as well as both upstream and downstream regions on the second chromosome. Kits may also be constructed for multiple translocation events or having more than two chromosomes involved according to the methods of the present invention.

Each probe is detectable when hybridized to the target DNA, preferably by being labeled with a unique detectable label that can be either directly or indirectly detected. The labeling may be by covalent bonding or other affinity attachment. Each polynucleotide comprising a probe is labeled with the same label and each probe has a detectably different label from other probes in the mixture. As such, one can easily detect each normal chromosome potentially involved in the translocation as well as fusions between the two or more breakpoint regions which are detected as a fusion signal.

The different construction of multiple fusion probes provides numerous advantages over two similarly labeled single fusion probes hybridizing to different locations. Some of these advantages were not apparent until after testing the probes on biological samples. Thus, by constructing probes complementary to the entire breakpoint regions, as in D-FISH, one achieves certain advantages over conventional S-FISH.

In the present invention's improved method, designated D-FISH, fusion signals can be detected in each cell as an indicator of the presence of a reciprocal translocation. The sensitivity of the method using the available S-FISH probes has not been sufficient in the past to detect very low levels of translocations which are found in the peripheral blood cells or bone marrows of many patients. Specifically, commercially available S-FISH detects about 70–75% of patients actually positive for the Philadelphia chromosome. Actual positive results were necessarily determined by sequencing, PCR amplification or Southern blotting. By contrast, using D-FISH with the probes of the present invention detects greater than 99% of patients actually positive. This data rivals or exceeds standard Q-cytogenetics (See Dewald et al data). The improved detection indicates that the present invention should be accepted as the "gold standard" by which all other assays are compared.

This improved sensitivity is accomplished by using probes which are specifically developed to cover the entire breakpoint region of each chromosome involved in the translocation. In such a translocation, the labeled probe for a first chromosome is immediately adjacent to the labeled probe for a second chromosome thereby producing multiple fusion signals. By contrast, S-FISH employs probes which are designed to be complementary to one side of each of two breakpoint regions and therefore relies upon the detection of a single fusion event.

The new method presented here involves novel DNA probe constructs which are designed to target the length of each breakpoint region in a translocation event and additional DNA sequence beyond both the 3' and the 5' ends of each breakpoint region. When the breakpoint region occurs in a gene, it is preferable for the probes to encompass the entire gene and additional DNA sequence beyond both ends also. When used together, all reciprocal translocation events involving the target gene regions can be detected simultaneously in an interphase or metaphase cell. The probes are further designed to give easily visualized balanced signals in interphase cells.

The effectiveness of dual or multi-fusion probes is perhaps best demonstrated when the DNA probes are fluorescently labeled in different colors and hybridized to cellular DNA using the standard assay technique of fluorescence in situ hybridization (FISH) (Pinkel et al, *Proc. Natl. Acad. Sci., U.S.A.* 83:2934–2938 (1986)). Various types of DNA probe configurations have been used with FISH technology in an attempt to find a reliable and sensitive assay for interphase cell analysis. However all of these techniques provide either too many false positives, false negatives or simply lack the sensitivity to determine the presence of the translocation in interphase detection of minimal residual disease and/or response to therapy. Additionally, other techniques are cumbersome or expensive to test or require large quantities of hard-to-obtain biological material. By comparison, the Examples below show obtaining a result from a simple blood sample using conventional cytogenetic equipment with a high sensitivity and low error rate.

Balanced and non-reciprocal translocations may also be detected using the probe strategy and method of the present invention. Even inversions within the same chromosome may be detected as double fusions with the probe sets developed for the two breakpoint regions on the same chromosome. In such situations, one still has two breakpoint regions forming at least one fusion site for detection of a fusion signal. The same general principles apply either way. In accordance with the present invention, probes constructed in accordance with the general instructions provided herein are used to produce reagents and a method for detecting multiple breaks as well as any resulting fusions thereby determining the presence of such multiple breakage events simultaneously. The present invention may also be used for screening for chromosome breakage at multiple genome sites due to environmental factors, chemicals, radiation (diagnostic X-rays or radiation therapy or radiation exposure), biological agents etc.

The source of cells may be highly variable. If a cancer is being diagnosed or monitored, cells from the tumor site or removed from the tumor site may be used. For inherited diseases, readily available cells from tissues, blood, urine, feces, buccal scrapings, cervical and vaginal scrapings (PAP smear), body fluids, etc. may be used. For prenatal testing, fetal, amniotic, placental, cord, chorionic villus, and "cells" including sperm or egg for the situations of gamete "donation" or in vitro fertilization may be used.

The cells being tested may be in any phase, but metaphase and interphase are preferred.

While this application generally refers to humans and human diseases, persons of skill will appreciate the invention is useful in other settings. The present invention is equally applicable to other animals for agricultural or veterinary purposes as useful in the diagnosis, prognosis and monitoring of disease. If so desired, the present invention is applicable to determining translocations in plants as well. The present invention is also applicable to non-disease conditions where determining the presence of a translocation is important for plant and animal breeding such as to follow the presence of a trait throughout generations.

One standard method for plant breeding involves infecting the plant with Agrobacterium tumefaciens carrying a Ti plasmid which will integrate T-DNA into the plant chromosome. Transfection of the plasmid per se may also be used. A desired gene is typically incorporated into the T-DNA region, especially in a hormone gene if not already deleted. In such a situation, the plant chromosome has a breakpoint region for inserted T-DNA. Probes encompassing the plant chromosome breakpoint region and the two ends of the T-DNA or the desired gene may be used to determine whether plant cells contain the desired gene. The present invention results in considerable time savings compared to tissue culture and cultivation of the plant to maturity and testing for a trait caused by the desired gene.

Along the same procedural lines, the present invention may be used to assay for insertion of any other DNA into a specific chromosome site such as is desirable in gene therapy. During certain forms of gene therapy, added DNA is incorporated into the host chromosomes at specific locations. The present invention permits monitoring and provides proof of integration.

Viruses which integrate are biologically significantly different when their DNA is integrated into a host chromosome. Such an integration involves a breakage of the chromosome and a fusion of the viral DNA into the chromosome. Monitoring the integration is an important step in assaying for antiviral therapeutics, determining prognosis, etc. If the integration site or region is known, probes to that site and to the virus (or viruses if two are coinfecting) may be prepared and used according to the present invention.

False positives can occur in normal cells, for example when the BCR locus of chromosome 22 coincidently occurs very close to, behind or in front of the ABL1 locus of chromosome 9. Since the cell being viewed is three dimensional and usually in interphase, the chromosomes are freely moving within the cell nucleus permitting a random juxtaposition of signal. About 4% of normal slides have the two loci sufficiently superimposed on each other to cause the signals to appear fused using S-FISH.

However, when using D-FISH, two fusion signals typically occur as well as two normal signals. The percentage of normal cells with both ABL1 and both BCR loci coincidently superimposed is very small. Thus, the false positive rate in D-FISH is lower. Still further, normal cells displaying two fusion signals by chance would not display two normal signals as well, providing a further check against false positives.

As for reducing the false negative rate and increasing sensitivity, one potentially has twice as many fusion signals per cell which makes it easier to detect an abnormal cell.

The advantages of the present invention depends upon a number of factors, including the unique probe configuration, the number or percentage of affected cells, which may vary with individuals and disease states. For example, the methods described above typically require that about 1% of the cells be affected for accurate signal detection. This compares to a S-FISH assay requiring about 30% of the cells positive. If fewer cells are affected, an abnormal condition may not be detected.

While the Examples use microscopic identification of normal and abnormal chromosomes, other techniques may be used. For example, cells may be observed and determined to contain or not contain a translocation during flow cytometry or extracts may be taken and conventional DNA hybridization assays performed.

Several factors determine how large a probe construct should be. In the example of the BCR gene, for example, the probe would be sufficiently long to include both the major breakpoint cluster region and the minor breakpoint cluster region, as well as sequences beyond the gene. For other genes exemplified below, the breakpoint region is widely variable in size and requires probes of sufficient size unique to each application and may be determined by routine optimization. Generally, the probes will have a considerable length complementary to the adjacent non-breakpoint region for a normal or translocated fusion configuration. The length will depend on the particular translocation being detected. The length of each probe will further be manipulated to make visually balanced signals and/or enough to routinely cause a color shift when the signal is fused to a different label's signal. The length must accommodate all breaks, regardless of where in the breakpoint region the actual breakage and fusion occurs. Preferably, the length is also be sufficient to provide fusion signals of similar size throughout the target clinical population of cells, thereby increasing reliability and ease of interpretation.

Generally, the length of the probe sets will correlate to the length of the largest breakpoint region involved in a translocation event. Thereby, the balance of fusion signals in interphase cells is assured. The length may also be affected by the amount of label which can be incorporated on the probe. Considerable variance is acceptable, if there is optimization of labeling conditions for each probe being developed.

In one preferred embodiment of the invention, one probe of a probe pair is designed to be complementary to the ABL1 sequence (600 Kb) and the other probe is designed to be complementary to the BCR sequence (500 Kb). Individual cloned human DNA probes of varying lengths complementary to the ABL1 and BCR breakpoint regions were used collectively to make probes of appropriate length. A single clone may be used; however, if the insert is of sufficient size. In practice, probes are developed from overlapping "probe sets", consisting of several cloned DNA sequences which hybridize to and span the breakpoints on the relevant chromosomes.

Alternative techniques may be used other than FISH for probes of the present invention. For example, during the use of conventional blot assays, Southern and Northern, probes of the present invention may be optimized to be used in lieu of other labeling techniques. The probes of the present invention may also be used in developing assays in aqueous solution.

The probes of the invention may be detected after it is hybridized to the target DNA or RNA. This may be done by any technique which detects a probe containing double stranded DNA within the biological sample. If the remainder of the sample lacks significant double stranded regions, one may use chemicals which specifically bind to double stranded but not single stranded DNA or DNA/RNA. Examples include a labeled antibody to double stranded DNA or RNA/DNA followed by detecting the label, ethidium bromide, SYBR green, an acridine dye (e.g. acridine orange), a protein or enzyme, etc.

The more preferred option is to have the probes labeled in order to provide a means of detection. Suitable labels include, but are not limited to, haptens and fluorophores, such as, FITC, Rhodamine and Texas Red as well as radioactive, chemiluminescent, bioluminescent, a metal chelator, quencher, enzyme, chemical modifications rendering the DNA detectable immunochemically or by affinity reactions, and other known labels. Many such suitable detection labels are known to persons of skill in the art of binding assays such as nucleic acid hybridization assays and immunoassays. When the label is a hapten, a receptor labeled directly or indirectly with an easily detectable substance, is employed before, with or after hybridization of the hapten labeled probe. When the label is a quencher, the absence of or reduced signal indicates the presence of the quencher.

Common ways to incorporate the label into the probe include nick translation, random priming or PCR amplification using a derivitized dNTP or NTP. Also post probe synthesis labeling and end labeling may be performed. The amount of label varies from one probe to another and the various uses for the probes. Too much labeling may actually cause a quenching effect. Typically about 1–25% of a nucleotide (A, G, C, or T) will be modified to incorporate a label into a DNA probe.

One of ordinary skill can choose appropriate labeling techniques, other colors or detection strategies which may vary depending on the particular translocation or other fusions being detected.

DEFINITIONS

As used herein, the term "probe" is intended to mean one or more polynucleic acids which hybridize specifically to a particular region of chromosome which is of interest. Depending on the size of the region, multiple polynucleotide molecules may be combined to comprise the probe. The number of polynucleotides will also be determined by whether the polynucleotides are synthesized chemically, by PCR, by plasmid, by cosmid, by yeast artificial chromosome (YAC) etc. Individual molecules comprising the probe may hybridize to overlapping portions of the chromosome of interest or may hybridize to physically linked regions separated from each other. These gaps may be sizable but should not be so large that upon hybridizing to a translocation locus in a cell, the probes are so far apart that they appear as non-associated signals and no fusion event can be reliably detected. For example, a 100 base pair gap is probably insignificant whereas a 1 Mb gap is too much to be acceptable. Note that the break may occur anywhere in the breakpoint region and therefore construction of the polynucleotide molecules composing the probe should be designed to accommodate breaks at the worst possible locations.

A probe need not have exact complementarity to the desired target, but should have sufficient complementarity to bind to the region of interest using the methods of the invention. To achieve this generally requires a matching sequence with at least 80%, preferably 95%, and most preferably about 100% complementarity to the target. Occasional polymorphisms may preclude true 100% complementarity in some individuals, particularly when the breakpoint does not occur in a coding sequence.

Accordingly, as used to refer to probes herein, the term "complementary" includes "substantially complementary" which is intended to refer to a probe which will specifically bind to the region of interest on a chromosome under the test conditions which are employed, and thus be useful for detecting and localizing the region. Complementarity will be extensive enough so that the probes will form specific and stable hybrids with the target DNA under the hybridization conditions used. Persons of skill in the art will be able to determine suitable sequences through the general knowledge available in the art, and by routine experimentation, using the examples set forth hereinbelow as guidelines.

A "cell" as used herein includes biological samples which were derived from cells. "Biological sample" includes all nucleic acid containing compositions where the nucleic acid (RNA or DNA, chromosome, viral, vector, mitochondrial . . . ) was obtained from an individual organism or amplified from a nucleic acid obtained from an individual organism. The slide preparation procedure used in the Examples actually kills the cell and removes some of its components. However, the DNA remains. The term "cell" as used herein includes cellular components, extracts and other partial cellular components provided that they contain the nucleic acids. It is preferred that a reasonably complete set of the chromosomes remains or at least the DNA of the breakpoint regions and adjacent regions remains such that one can determine normal untranslocated DNA sequences from fused DNA sequences resulting from a translocation.

A "translocation" is the exchange of genetic material between two or more non-homologous chromosomes. This is frequently a reciprocal event where two chromosomes are simultaneously broken and the fragments are exchanged between the two chromosomes. Two new chromosome derivatives are created.

A piece of a chromosome may be broken twice and reincorporated in the same region in reversed order. This is called a inversion and is a subset of structural abnormalities caused by chromosomal breakage and rearrangement.

The present invention has many uses other than detecting reciprocal translocations such as detecting other chromosomal abnormalities caused by chromosomal breakage and rearrangement such as insertions, inversions, derivative chromosomes and possibly duplications and ring formations.

As used herein, the phrase "the entire breakpoint region" is intended to refer to a sequence or probe of sufficient length to include the entire region in which a particular break may occur. This region will vary with the particular structural aberration one wishes to detect. In rare instances where the boundaries of the breakpoint region may not be completely known or unclear, the breakpoint region is the region encompassing the distribution of two standard deviations of known breakpoints.

A "contig" is a collection of two or more overlapping cloned DNA fragments that when used together will extend the target region beyond that of using a singular cloned fragment. A contig refers to "contiguous" DNA fragments.

EXAMPLE 1: CONSTRUCTION OF BCR/ABL1 DUAL FUSION PROBES

The BCR/ABL1 dual fusion probes were assembled by screening through several different human libraries cloned into PAC, P1, BAC, and YAC vectors available from commercial sources, e.g. a CEPH library. The procedure included several rounds of sequencing and walking. These methods are known to persons of skill in the art and are described in various molecular procedure manuals such as PCR Protocols, A Guide to Methods and Applications, Innis et al, Academic Press, Inc. (1990) incorporated herein by reference.

Each round of screening included the following steps:
1. Synthesizing new PCR primers based on sequence information.
2. Establishing PCR conditions for the new primers.
3. Screening the libraries by either PCR (using primers) or DNA hybridization (by amplified fragments).
4. Selecting the positive clones.
5. Evaluating the positive clones by FISH. Verifying that the positive clone hybridizes to the correct region and does not show any cross hybridization.
6. Obtaining the end sequences of the insert of new clones by either direct sequencing or by sequencing the purified end fragment amplified by using a combination of Alu or other primers and vector end primers.
7. Comparing the new sequence to the existing sequence to establish the relative location of the new clone. New primers were then made from the new sequence outside the existing sequence.
8. Repeating steps 2–7 until the probes reached the appropriate length to include the entire breakpoint region and achieve the desired FISH signal intensity.
9. Establishing the relative locations of all clones in the final contig by STS mapping and estimating the size of the contig.

To obtain multiple fusion probes according to the invention, it is preferred that the probes cover both sides of the breakpoint and show not only good but also balanced signals in affected cells. For both BCR and ABL1 probes, screening was done for clones which collectively hybridize to the entire breakpoint region and both sides of the breakpoint region containing normal chromosomal DNA.

BCR:

The BCR dual fusion probe set is composed of 5 human PAC clones which are shown in Table 1, FIG. 7.

The BCR region contains a 152141 bp sequence published by GenBank. Three primer pairs were initially made, BCR a/b, BCR c/d, and BCR e/f, which correspond to the gene sequence at the −15 kb, −123 kb and −152 kb, 5' to 3' positions respectively. These primer sets were used to screen a P1 library by PCR and the amplified fragments were isolated and pooled to screen a PAC library by hybridization. Several positive P1 and PAC clones containing BCR gene sequences were obtained.

P1 Clone OC2001 was scored positive using primers BCR a/b. The end sequences of the insert were obtained. This clone has one end of the insert located in the BCR known sequence and one end outside the 5' end of known sequence. Primer set BCR 13/14 was synthesized using the new sequence information. Both PAC OCB1001 and OCB1002 were obtained by screening using BCR 13/14. The next round of screening was done by first sequencing the end sequences of the insert in PAC OCB1001, establishing the 5' and 3' positions of the ends and primers BCR 26/27 were made. PAC OCB1003 was acquired by screening the PAC library using the new primers BCR 26/27. This PAC is on the most 5' end of the contig.

PAC OCB1004 was obtained from the hybridization of PAC library using the pooled amplified DNA fragments generated by the BCR a-f primers described above. This clone covers almost all the BCR known sequence and also extends in the 3' direction.

From the PCR screening of the P1 library using primers BCR e/f, P1 clone OC2002 was obtained on the 3' end of the gene. Both ends of the insert were sequenced. This clone contains the BCR gene sequences from the 3' position, 109 kb into the gene, and extends further in the 3' direction from the end of the BCR gene. A new primer pair BCR 13/14 was made using the new 3' end sequence. PAC OCB1005 was obtained from the new screening which became the furthest 3' clone in the contig.

The size of the inserts of these individual clones are estimated by adding up all the EcoR1 restriction fragments found on agarose gel as compared to commercially available molecular weight DNA markers. The relative locations of all the clones are established by whether the clones are positive or negative to all the PCR primer sets tested. Because the entirety of the clones were not sequenced, the extent of overlap or gaps (if any) present in the clones has not been characterized. However, the clones are known to contain sequences in common to other clones within the BCR probe set. The total size of the BCR contig is approximately 500 kb.

ABL1

The ABL1 dual fusion probe set consists of 1 BAC, 1 P1, 4 PAC and 1 YAC clone as shown in Table 2, (FIG. 8).

The ABL1 region contains 3 segments of published GenBank sequences: HSALBGR1, 35,692 bp, covering the 5' ABL1 exon 1b and part of intron 1b, HSABLGR2, 59,012 bp containing portions of intron 1b and HSABLGR3, 84,539 bp extending from the end of intron 1b to the end of exon 10 and poly A region. The intron 1b is about 200 kb in length.

The initial screening was done in a similar way to screening for five BCR probes. Three primer sets were synthesized, ABL1 a/b, ABL1 c/d, and ABL1 e/f. ABL1 a/b is located >2000 bp in from the 5' end of the HSALBGR1 sequence, see table 2, FIG. 8. ABL1 c/d is ~79,000 bp in from the 5' end of the HSABLGR3 sequence, and ABL1 e/f is located ~31,000 bp in from the 5' end of HSABLGR2 sequence. The ABL1 a-f primers were used to screen a P1 library directly by PCR and the amplified fragments from these primers were used to screen a PAC library by DNA hybridization. Several positive P1 and PAC clones were identified.

The P1 clone OC3001 was obtained from PCR screening using primers ABL1 a/b. The clone covers a small segment of the HSABLGR1 sequence and extends further in the 5' end of ABL1. A new primer set ABL1 5/6 was made after sequencing the end of the OC3001 insert. ABL1 5/6 was used to screen a PAC library and the PAC clone OCA1001 was acquired. The OCA1001 clone contains the most 5' end of the contig. The P1 clone OC3002 was obtained by PCR screening using primers ABL1 e/f. This clone contains most of the HSABLGR1 and HSABLGR2 sequence regions.

PAC clone OCA1002 was obtained by hybridization screening using the pooled amplified fragments generated by the ABL 1 a-f primers. This PAC clone also extends outside the 5' end of ABL1 gene. The end fragments of the insert were sequenced and primer set ABL1 3/4 was made. ABL1 3/4 was used to screen a BAC library. The BAC clone OCA1003 was identified.

YAC clone OCA1004 was obtained from the commercially available library. OCA1004 contains a portion of HSABLGR2 sequence and extends beyond the 3' end of the HSABLGR3 region. The end fragments of OCA1004 were isolated and sequenced. Primer pair ABL1 7/8 was made and used to screen a PAC library. PAC clone OCA1005 was obtained. A new primer set, ABL1 19/20, was synthesized using sequence information obtained from clone OCA1005. Both PAC OCA1006 and OCA1007 were identified by library screening using ABL1 19/20.

The sizes of the inserts of the clones in the ABL1 probe set, except for the YAC, were estimated by summing up EcoR1 restriction fragments visualized on an agarose gel. The size of YAC clone was determined by comparing to known size standards on a gel. The relative positions of all the clones were determined from using the primer sets developed for screening DNA bands as physical map anchor sites throughout the ABL1 region. The total length of this contig is approximately 600 kb.

The combination of the BCR and ABL1 probe sets described above defines a dual fusion probe set for t(9;22). It has been designated P5161-DC. The skilled artisan will appreciate that by using these and other techniques known in the art, additional suitable probe sets would be constructed for the ABL1/BCR translocation and for other translocations of interest.

EXAMPLE 2: USING THE PROBE SET FOR CML D-FISH ASSAYS

The P5161-DC probe set was used in standard FISH protocols to devaluate the usefulness of using dual fusion probes (D-FISH) FOR DETECTION. The study of Philadelphia chromosome in a CML clinical population included 37 paired-sets of bone marrow and peripheral blood specimens from 10 patients undergoing treatment for CML, 10 normal peripheral blood specimens, 10 normal bone marrow specimens and four serial dilutions with known percentages of Ph positive nuclei.

Each patient with CML was a participant of the CML National Study Group clinical trial and was randomly receiving treatment with interferon α-2b with or without ara-C. Each patient was known to have cells with a Ph chromosome that produced a typical D-FISH pattern (two fusion signals, two normal signals) for t(9;22)(q34;q11.2). For each patient a paired-set of bone marrow and peripheral blood specimens were collected prior to treatment and at two or more times at approximately 4-month intervals during treatment. Each paired-set of peripheral blood and bone marrow specimens was obtained on the same day except for specimens collected prior to treatment in patients 3 (blood and bone marrow were collected 1 day apart), 5 and 8 (blood and bone marrow were collected 4 days apart).

Uncultured bone marrow and peripheral blood specimens were processed by conventional procedures for cytogenetic and FISH studies. These specimens were stored as fixed pellets at −70° C. in methanol:acetic acid (3:1) until FISH studies could be performed. The D-FISH specimens were prepared by being washed twice with fresh fixative and cells were placed on microscope slides and allowed to air-dry in a CDS-5 cytogenetic drying chamber (Thermotron, Holland, Mich.) adjusted to 50% relative humidity and 25° C. Slides were further dried for 1 hr in a 65° C. oven and then treated with 2× standard saline citrate solution (SSC) (300 mmol/L sodium chloride, 30 mmol/L sodium citrate) for 1 hr at 37° C. Slides were then dehydrated with 70–85–100% cold ethanol (stored at −20° C.) for 2 minutes each, and air-dried.

The FISH hybridization and detection procedure was carried out as follows. Chromosomal DNA (in the form of cells on a slide) was denatured in 70% formamide/2×SSC for 2 min at 70° C. Slides were dehydrated with an ethanol series (70%, 85% and 100%) for 2 min each and air-dried. The probe (Oncor product #P5161-DC) was denatured in a water bath at 70° C. for 5 min. Then 10 μl of stock solution BCR/ABL1 probes were added to each slide, a 22×22 mm coverslip placed on the slide and sealed with rubber cement. Slides were hybridized for 18–20 hrs at 37° C. in a humidified chamber. After the coverslips were removed, slides were washed for 2 min in 0.4×SSC at 70° C., and then in 1× PBD (phosphate-buffered non-ionic detergent) for 2 min. Chromatin was counterstained in blue with 10 μl of 1% solution of 4′,6′-diamidine-2-phenylindole (DAPI) in Vectashield antifade. Representative cells were captured using a computer-based imaging system (Quips XL Genetics Workstation, Vysis, Inc., Downers Grove, Ill.).

Q-cytogenetic studies were performed on each bone marrow specimen by analyzing 25 consecutive G-banded or Q-banded metaphases in which chromosomes 9 and 22 could be observed using the methods of Dewald et al, *Cancer Cytogenet*. 94:59 (1997). Hypermetaphase studies using single fusion probes for BCR and ABL1 (S-FISH) were done on many of these specimens using the methods of Seong et al, *Blood* 86:2343 (1995). D-FISH was performed using the directly labeled P5161-DC probe set to reveal two BCR/ABL1 fusion signals in cells with a t(9;22)(q34;q11.2); one on the abnormal chromosome 9 and the other on the abnormal chromosome 22. The ABL1 (600 kb) probe was directly labeled with Rhodamine Green (green signal) and included several DNA sequences that hybridized to 9 q34 and spanned the 200-Kb breakpoint region of ABL1 including additional normal chromosome sequence on each side of the breakpoint region. The BCR (500 Kb) probe was directly labeled with Texas Red (red signal) and included several DNA sequences that hybridized to 22q11.2 and spanned the common breakpoints in both the major and minor BCR as well as normal chromosome sequences on each side of the BCR gene breakpoint regions.

The specimens were studied in random order and in a blind fashion by two microscopists using strict scoring criteria for D-FISH. Dewald et al, *Blood* 31(9): 3357–3365 (1998). As referred to hereinafter, red BCR signals are referred to as R, green ABL1 signals as G, and BCR/ABL1 fusion signals as F. For scoring purposes, fusion signals were defined as merging or touching R and G signals. The scoring process was limited to normal nuclei with 2 R2 G, and abnormal nuclei with 1R1G2 F or 2R2G1F (one Ph chromosome), and 1R1G3F or 2R2G2F (two Ph chromosomes). For each specimen, each microscopist scored 250 consecutive qualifying interphase nuclei from different areas of the same slide. At the conclusion of the study, the inter-microscopist agreement was sufficient to pool their results on each specimen in subsequent analyses of the data. Thus, the final statistical analyses were based on 500 nuclei per specimen.

The normal range for D-FISH was calculated for peripheral blood specimens collected from 10 patients without any malignant hematologic disorder and for bone marrow specimens collected from 10 normal bone marrow transplant donors. The four serial dilutions were prepared by mixing cells from a normal individual and a Ph positive specimen to create a series of specimens determined by repeated blind studies to contain specified mean percentages of Ph positive nuclei.

The D-FISH results for each patient's specimens from both peripheral blood and bone marrow samples were calculated as the proportion of abnormal cells (number of abnormal cells per 500 scored cells). Since the proportion (p) of abnormal cells among the specimens ranged from 0 to 1 (i.e. 0–100%), a $\sin^{1}(\sqrt{p})$ transformation was used to stabilize variances and provide a more nearly Gaussian distribution of values. Then, the differences (delta value) between bone marrow and peripheral blood in transformed proportions were computed for each patient's specimens. The proportion (p) of abnormal cells by Q-cytogenetics was also transformed to $\sin^{1}(\sqrt{p})$.

The delta value for each paired-set of bone marrow and blood specimens was then analyzed using a repeated measures regression analysis (PROC MIXED in SAS) (19). For purposes of this statistical analysis, the approximate 4 month sampling intervals relative to commencement of therapy was considered a nominal predictor variable and the transformed proportion from Q-cytogenetics was included as a covariate. The within-patient correlation of delta values among respective specimen collection times was specified as an autocorrelation structure depending on the actual number of days between sampling times i.e., smaller correlations between sequential values for longer times between sampling episodes.

The classification scheme for response to therapy was based on Q-cytogenetics and was similar to the Italian Cooperative Group (Italian Cooperative Study Group on Chronic Myeloid Leukemia *New England Journal of Medicine* 30:820 (1994)) i.e., no response, minimal, minor, major and complete remission when 100%, 99–67%, 66–33%, 32–1% and 0% of metaphases are Ph positive, respectively.

Probe Sets in a D-FISH Assay Demonstrate Higher Sensitivity Than Standard Cytogenetic Testing The goal was to study the effectiveness of the P5161-DC probes using 500 nuclei for each bone marrow and blood specimen. The goal for Q-cytogenetics was to study 25 metaphases from each bone marrow specimen. The goal for hypermetaphase studies was to study 200 metaphases from bone marrow. D-FISH was successful on 37/37 blood specimens and 37/37 bone marrow specimens. Q-cytogenetic was successful in 32/37 bone marrow specimens. Hypermetaphase was successful in 14/24 bone marrow specimens.

Very Low False Positive Rate (<1.0%)

Based on 500 nuclei from each of 10 normal bone marrow specimens, the mean percentage and standard deviation of nuclei with false BCR/ABL1 fusion was 0.1%±0.1 (range 0 to 1 per 500 nuclei). Based on 500 nuclei from each of 10 normal peripheral blood specimens, the mean percentage and standard deviation of nuclei with false BCR/ABL1 fusion was 0.04%±0.08. Based on this data, the upper bound of a one-sided 95% confidence interval for observing 1 to 500 (0.2%) neoplastic cells in either bone marrow or peripheral blood was calculated using the binomial distribution. For both bone marrow and peripheral blood, this calculation implied a cutoff greater than 4/500 (>0.8%) nuclei with BCR/ABL1 fusion to classify any specimen as abnormal.

Abnormal Reference Range for D-FISH in Untreated CML

The results of D-FISH for specimens from seven patients (nos. 2–7, 9) that were collected prior to treatment and that were not mosaic by Q-cytogenetic studies were used to establish an abnormal reference range. These specimens generally represent patients with untreated CML in clinical practice. Among these seven specimens, the mean percentage of abnormal cells was 97.6%±1.38 (range 95.4 to 99.0) for bone marrow, and 86.1%±13.59 (range 61.6 to 98.5) for blood.

Serial Dilutions

The observed percentage of neoplastic cells in each of the four serial dilution specimens was 97.6, 49.2, 8.2 and 1.8. The expected mean percentage of neoplastic cells in these specimens was 98.2, 49.1, 10.7, and 2.8, respectively. The difference between observed and expected values for each of these specimens was 0.6%, 0.1%, 2.5% and 1.0%, respectively.

Results of Using the Probe Set in a D-FISH Assay With Clinical Specimens

Figure 3:
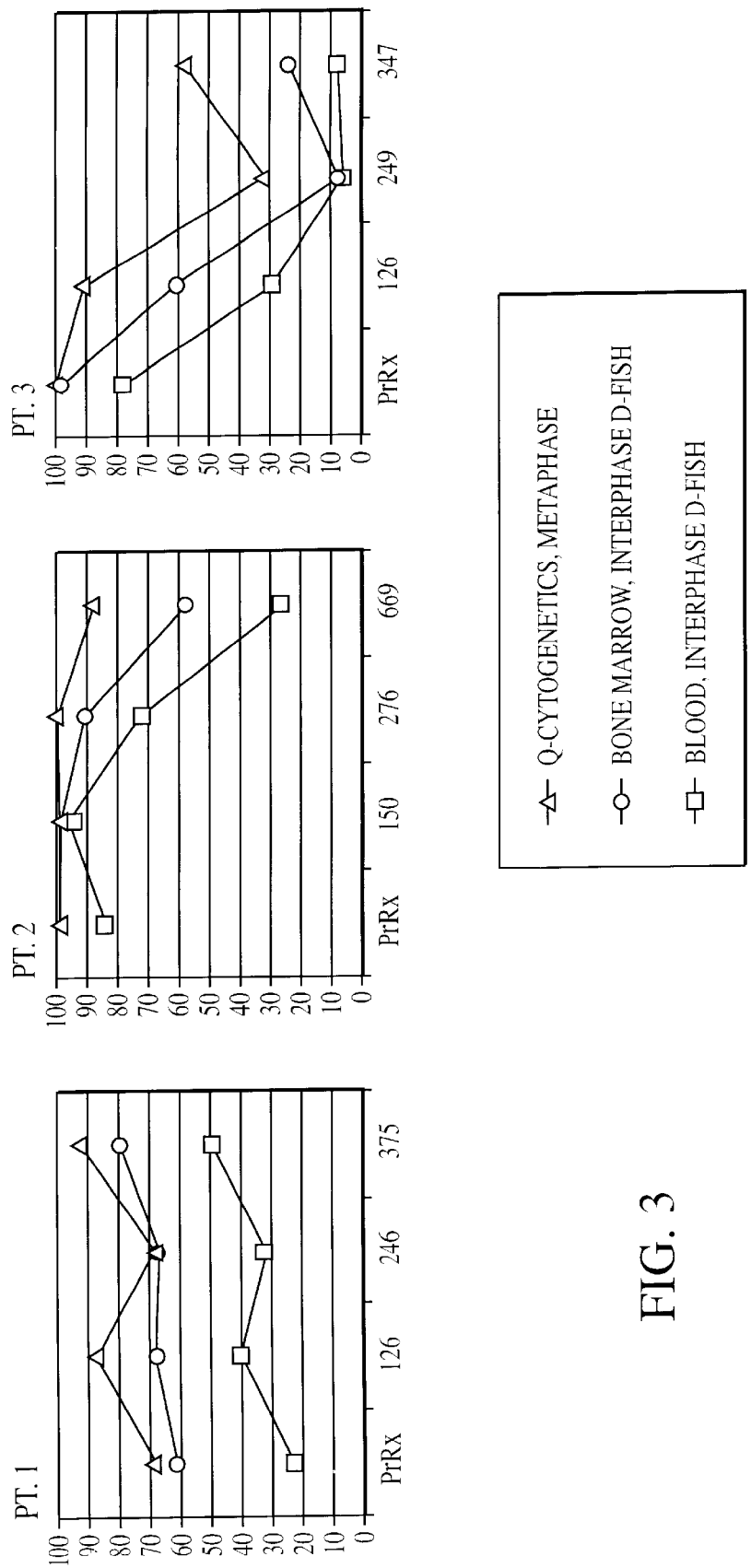
FIG. 3. Percentage of Ph positive cells (Y-axis) prior to therapy and during treatment at approximately 4 month sampling intervals (X-axis in days) in bone marrow by Q-cytogenetics and D-FISH, and blood by D-FISH.

Results for Q-cytogenetic studies for bone marrow, and D-FISH for bone marrow and blood for each patient specimen are shown in FIG. 3. Based on Q-cytogenetics, three patients (nos. 4, 5 and 6) achieved a complete cytogenetic remission, one patient (no. 3) briefly achieved a major response and the rest of the patients were classified as minimal, minor or non-responders.

Each bone marrow specimen that had any abnormal metaphases by Q-cytogenetics was also abnormal for interphase nuclei by D-FISH in blood and bone marrow. Six specimens from three patients (nos. 4, 5 and 6) had only normal metaphases by Q-cytogenetics. For patient 6, D-FISH results were abnormal at 357 days in both bone marrow (4.8% abnormal nuclei) and blood (3.0% abnormal nuclei). For patient 5 at 262 days, the peripheral blood was marginally abnormal (1.0% abnormal nuclei) but bone marrow was within normal limits (0.6% abnormal nuclei). Each of the remaining four specimens with only normal metaphases by Q-cytogenetics were within normal limits for D-FISH in both bone marrow and blood.

Detection of Minimal Residual Disease States and Tracking Response to Therapy using the Probe Sets in FISH Additional studies on the paired-sets of bone marrow and blood specimens that were normal by Q-cytogenetics and D-FISH were done to look for minimal residual disease. In a blind study, D-FISH was used to score 6,000 nuclei from four of the bone marrow specimens and five of the peripheral blood specimens in this series (Table 3, FIG. 9), and 3 blood and bone marrow specimens from normal individuals. In a separate study, the normal range for D-FISH for 6,000 nuclei was calculated to be <0.079%. Based on this cutoff, each of the normal blood and bone marrow specimens was correctly classified as normal. Three of the four patient bone marrow specimens and each of the patient peripheral blood specimens had minimal residual disease. It was not possible to do further studies on bone marrow no. 5 from patient 4 as this specimen had no leftover cells. The paired-blood specimen for this sampling time was in the abnormal range for D-FISH when 6,000 nuclei were studied and the bone marrow and one Ph positive metaphase among 169 metaphases that were examined by hypermetaphase FISH studies.

The actual proportions of neoplastic cells from bone marrow specimens were plotted against the corresponding proportions from peripheral blood samples (FIG. 2). The results imply that the proportion of abnormal cells from bone marrow specimens was typically greater (above y=x line) than for peripheral blood.

For D-FISH, the mean 4 month inter-sample differences in percentage of abnormal nuclei between paired-sets of bone marrow and peripheral blood were not statistically different (p>0.3)(Table 4, FIG. 10). The deltas for D-FISH for peripheral blood were associated (p<0.05) with the transformed proportion of abnormal cells based on Q-cytogenetics of the paired bone marrow specimen. This is important because Q-cytogenetics of bone marrow is widely recognized as the "gold standard" for monitoring response to interferon therapy.

Figure 4:
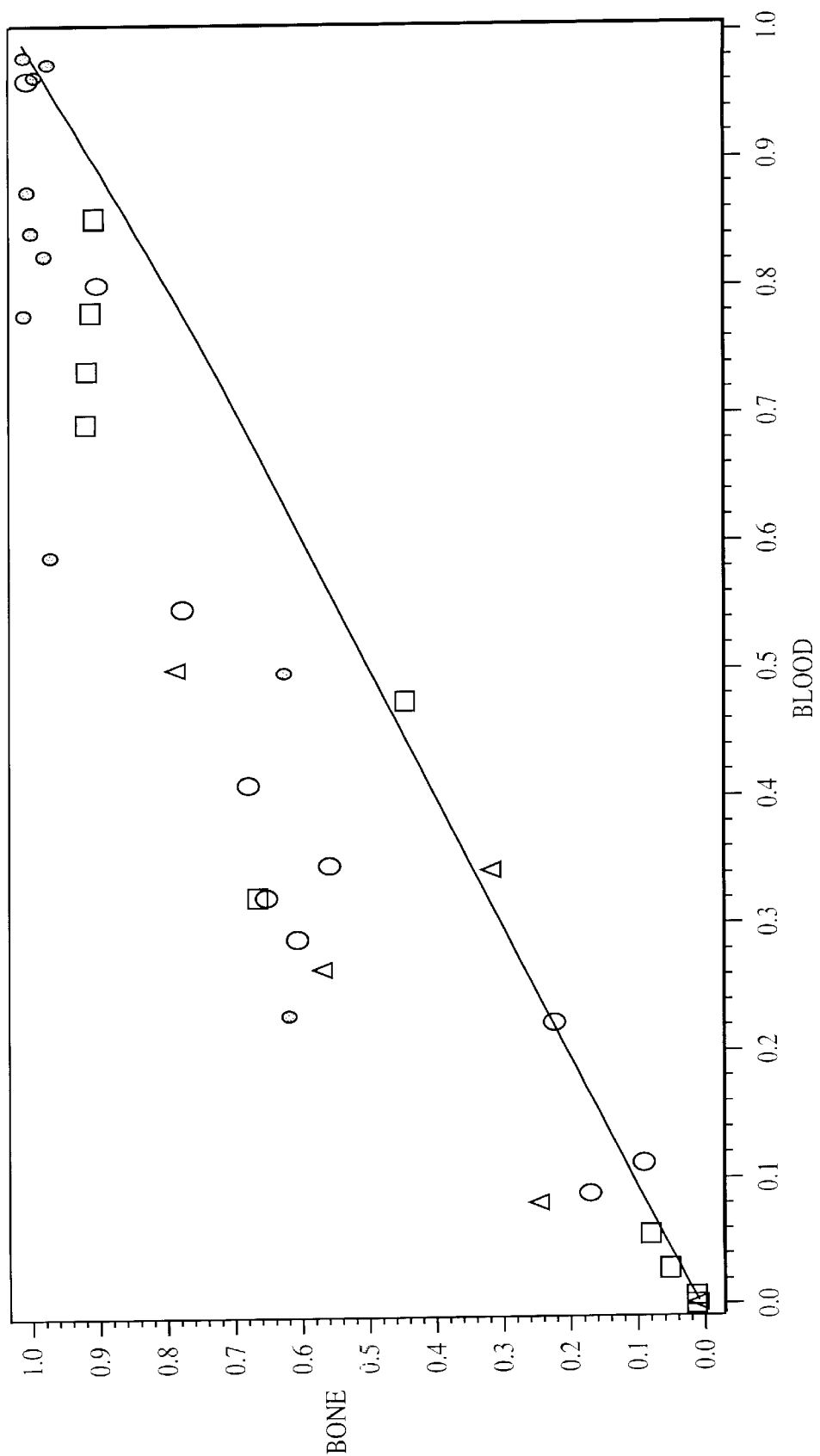
FIG. 4. Relationship between the percentage of Ph positive cells for paired-sets of bone marrow (Y-axis) and peripheral blood (X-axis).
Figure 5:
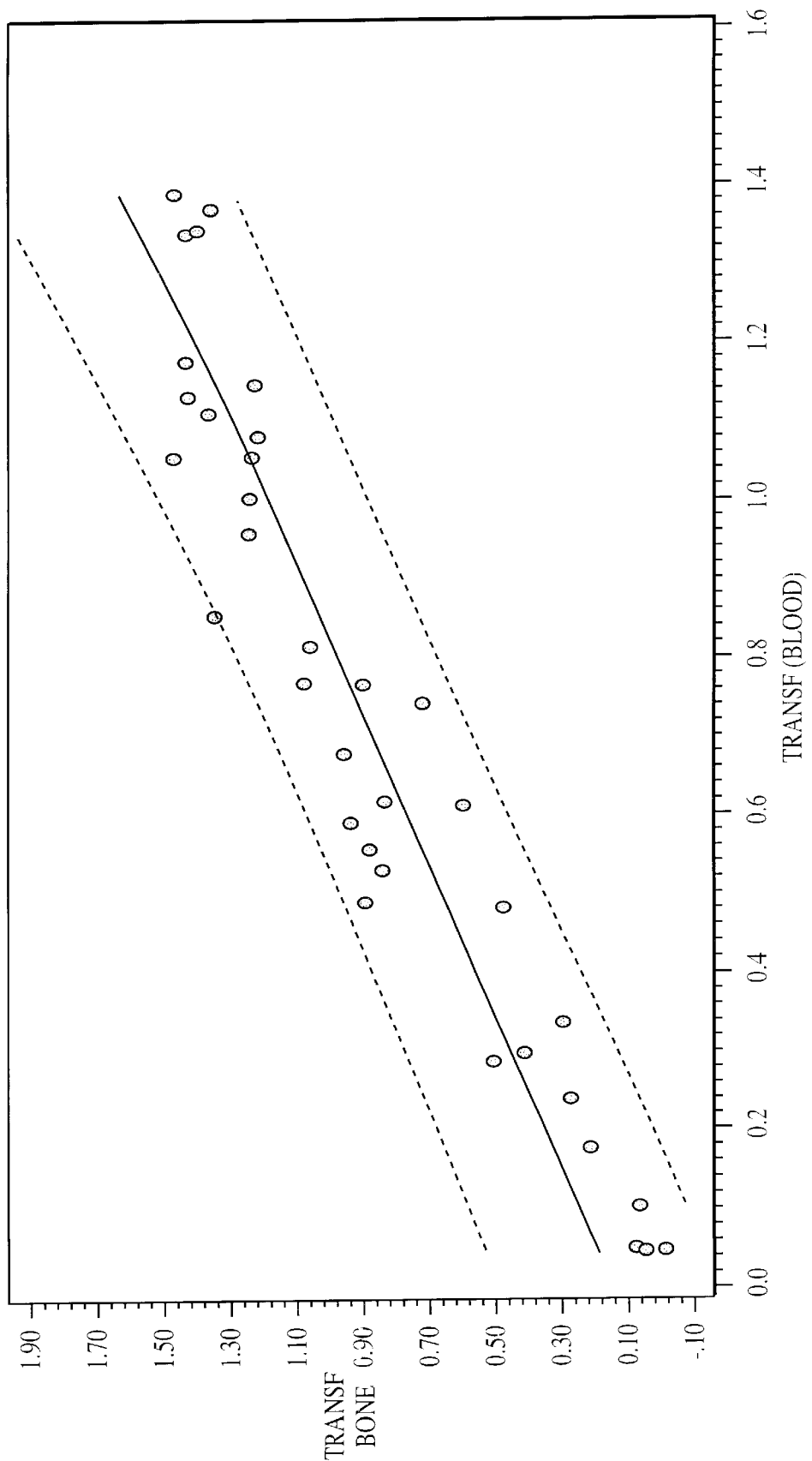
FIG. 5. Linear regression analysis of the (transformed) proportion of abnormal cells from bone marrow on the (transformed) proportion from peripheral blood from FIG. 4. Dashed lines are the 95% prediction interval.
Figure 6:
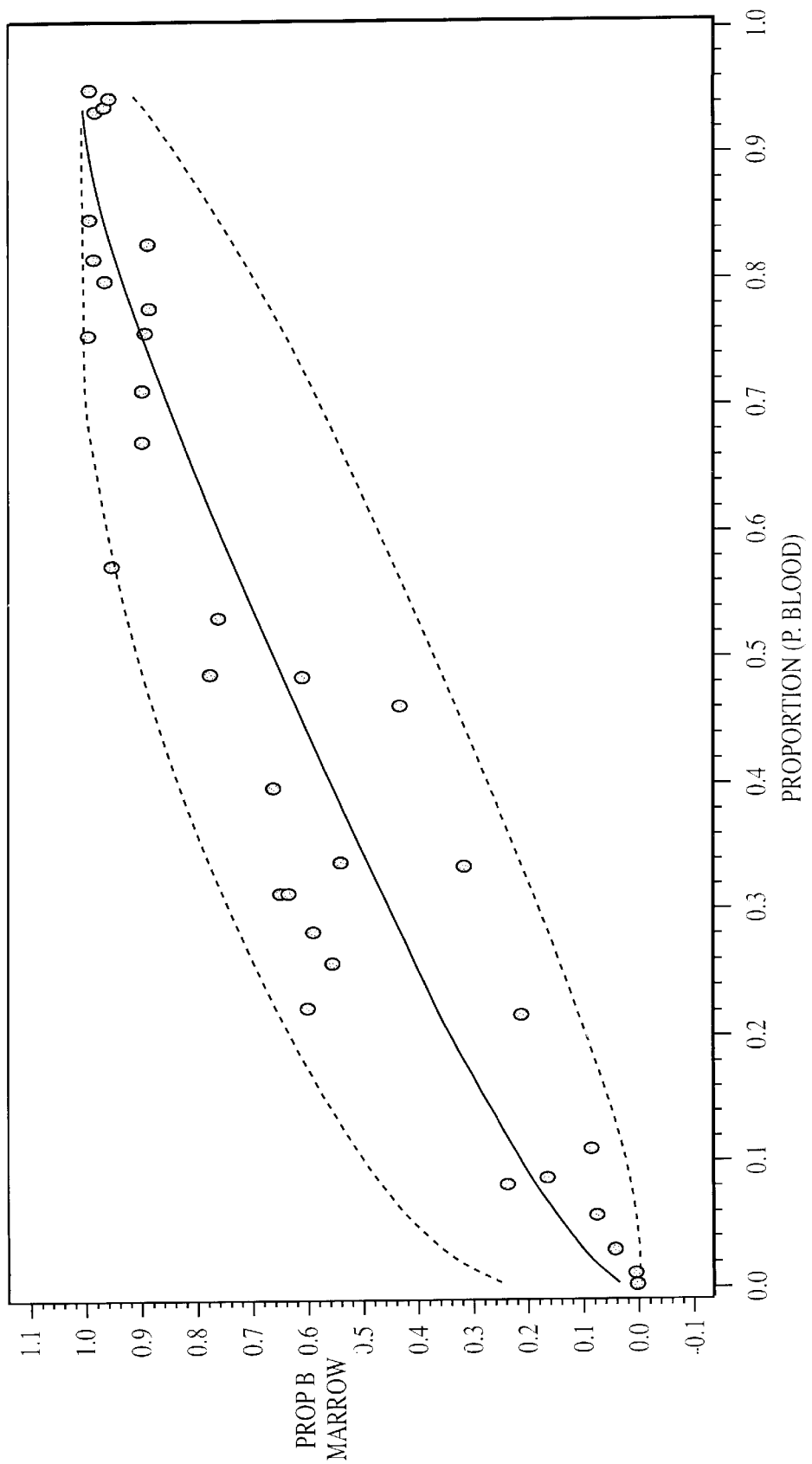
FIG. 6. Results of linear regression analysis but transformed to original scale of proportions of abnormal cells for bone narrow (Y-axis) versus peripheral blood (X-axis). Dashed lines represent the 95 prediction internal for a bone narrow prediction given a specific peripheral blood score.
Figure 3:
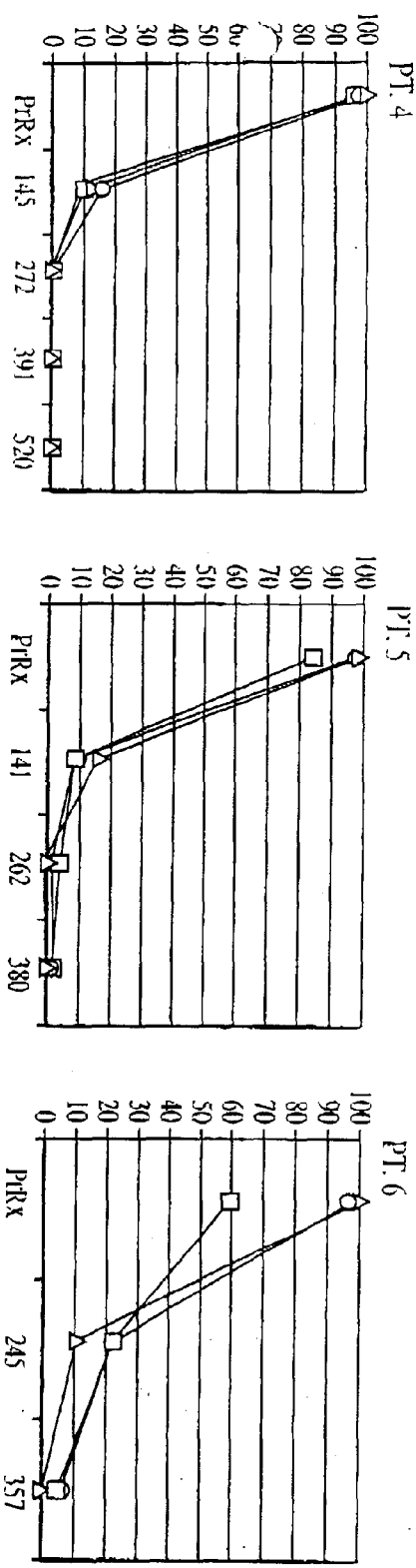
Figure 3:
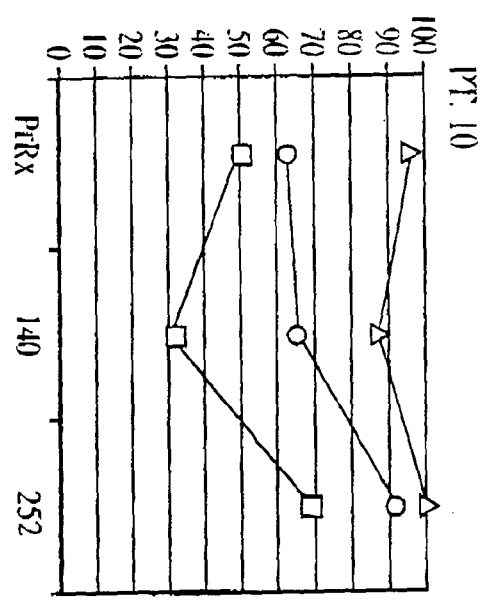

Based on these results, an additional regression analysis was done to develop a model for estimating the proportion of abnormal cells that would be obtained from bone marrow specimens using D-FISH results from peripheral blood samples. This is regression analysis of the data displayed in FIG. 4, but used the transformed values of the proportions (FIG. 3). In FIG. 5, the dashed lines represent an approximate 95% confidence interval for a new predicted observation given a (new) peripheral blood value (prediction interval). This analysis indicated a significant (p<0.001) linear relationship and yields the following equation for estimating the proportion of abnormal cells in bone marrow specimens ($P_{BM}$), $\hat{P}_{BM} = [\sin\{0.1494 + 1.0324 \ast \sin^{-1}(\sqrt{P_{PB}})\}]^2$, where $P_{PB}$ is the proportion of abnormal cells based on D-FISH results in peripheral blood samples. This relationship is displayed in FIG. 6, and the numeric results for several choices of $P_{PB}$ is listed in Table 5.

Discussion

The 4-month inter-sample changes in percentage of neoplastic nuclei in blood agreed closely with the corresponding intersample changes in percentage of neoplastic metaphases and nuclei in bone marrow over the course of interferon α-2b therapy. The reduction in percentage of Ph positive metaphases correlates with a prolonged chronic phase and increased survival in CML and the results of D-FISH on blood correlates with Q-cytogenetics. This demonstrates that using probes according to the present invention in a FISH assay is efficacious to test periodic peripheral blood specimens from patients with CML to monitor the effectiveness of interferon therapy. The analysis of 500 nuclei with the P5161-DC probe set in a D-FISH in bone marrow and peripheral blood detects <1% disease and is at least as sensitive as Q-cytogenetics. Thus, D-FISH analyses of interphase nuclei using probe constructs according to the present invention could substitute for Q-cytogenetics for purposes of monitoring response to therapy for CML. By analyzing 6,000 nuclei in specimens that were normal by Q-cytogenetics and by D-FISH based on analysis of 500 nuclei revealed evidence of residual disease was found (Table 4, FIG. 10). Thus, the methods and probe sets of the invention have the potential to detect very low levels of minimal disease in both blood and bone marrow.

In one other experiment that compares the results of FISH studies of paired-sets of bone marrow and peripheral blood to monitor therapy in CML, Muhlmann et al, *Genes, Chromosomes and Cancer* 21:90 (1998) used S-FISH to study 49 peripheral blood smears and 30 bone marrow specimens from 36 patients in chronic phase CML at different stages of cytogenetic remission. This experiment establishes that one can use whole blood as a comparative measure for events in the bone marrow.

The present invention precisely predicts the percentage of neoplastic nuclei in bone marrow based on data from blood. This should allow one to use blood to monitor therapy in clinical practice. The results presented in the present specification indicate that it is best to assess response to therapy based on changes in percentage of neoplastic nuclei using the same tissue over time. In other words, to compare D-FISH results among blood studies or among bone marrow studies, but not between blood and bone marrow studies. This is important because the percentage of abnormal nuclei in blood and bone marrow differs in most patients at most times before and after therapy (FIG. 4).

The results show a strong correlation between changes in the percentage of Ph positive metaphases by Q-cytogenetic studies over the course of therapy and changes in the percentage of interphase nuclei with BCR/ABL1 fusion in both blood and bone marrow. D-FISH using the probes of the invention was also useful to identify residual disease in both bone marrow and peripheral blood specimens for patients in complete cytogenetic remission. For patients on therapy, D-FISH could then be performed on peripheral blood at periodic intervals to assess the effectiveness of therapy. Consequently, bone marrow would not need to be collected to monitor therapy as frequently or at all as it is in current practice.

More details regarding scoring and correlation to clinical patients may be found in Dewald et al, Blood 31(9): 3357–3365 (1998).

EXAMPLE 3: CONSTRUCTION OF AML1/ETO DUAL FUSION PROBES

The AML1/ETO also called MTG8/CDR dual probes were assembled using the same method as in EXAMPLE 1 above. The highlights being illustrated below. The breakpoints are known to be clustered, Miyoshi et al (1991), Erickson et al (1992), Shimizu et al (1992), and Tighe et al (1993). The translocation has traditionally been detected using reverse transcriptase mediated polymerase chain reaction.

Two overlapping YACs, 902G10 and 903A9 were isolated from a total human library using an ETO cDNA probe. The YACs spanned the entire 8q22 breakpoint region. YAC C14B2 is predominantly located proximal to the 21q22 breakpoint region. YAC 925E1 was obtained from a total human library and includes a region located immediately distal to the breakpoint region.

The YAC DNAs 902G10 and 903A9 were labeled by nick translation with digoxigenin and C14B2 and 925E1 were labeled with biotin. FITC was used to detect biotin labeled probe molecules and rhodamine was used to detect digoxigenin labeled probe molecules using detection kits (Oncor, Inc.)

EXAMPLE 4: D-FISH FOR THE AML1/ETO TRANSLOCATION

The methods of Example 2 were repeated using the probe set of Example 3 with AML cell line Kasumi-1, lymphoblastoid cell line GM09948, bone marrow. Excellent results were obtained either two clear fusion signals being seen in a large percentage of cells. Details may be seen in Paskulin et al, Genes, Chromosomes & Cancer 21:144–151 (1998). The method of Example 2 is also performed on peripheral blood cells and correlated to the bone marrow data.

References cited herein are hereby incorporated by reference, and are listed below for convenience:

REFERENCES

Bentz, M., Cabot, G., Moos, M., Speicher, M. R., Ganser, A., Lichter, P. and Dohner, H. (1994) *Blood* 83: 1922.

Chumakov et al, *Nature* 377:175–197 (1995).

Dewald, GW, Juneau, AL, Schad, CR, Tefferi, A *Cancer Cytogenet.* 94:59 (1997).

Dewald et al, *Blood* 31(9): 3357–3365 (1998).

Fischer et al, *Blood* 88: 3962–3971 (1996).

Italian Cooperative Study Group on Chronic Myeloid Leukemia *New England Journal of Medicine* 30:820 (1994).

Kurzrock et al, *New England Journal of Medicine* 319:990 (1988).

Le Beau, *Blood* 81: 1979–1983 (1993).

Lion, T, Monitoring of Residual Disease in Chronic Myelogenous Leukaemia: Methodological Approaches and Clinical Aspects *Leukaemia* 10: 896 (1996).

Muhlmann, J., Thaler, H. Hilbe, W, Bechter, O, Erdel, M., Utermann, G. Duba, HC *Genes, Chromosomes and Cancer* 21:90.(1988).

Nakane et al, *Acta Histochem. Cytochem.* 20(2):229 (1987).

Pinkel et al, *Proc. Natl. Acad. Sci., U.S.A.* 83:2934–2938 (1986).

Paskulin et al, *Genes, Chromosomes & Cancer* 21:144–151 (1998).

Rudkin et al, *Nature* 265:472–3 (1977).

Sacchi et al, *Cancer Genetics and Cytogenetics* 79: 97–103 (1995)

Sinclair, P. B., Green, A. R., Grace, C., Nacheva, E. P., *Blood* 90:1395 (1997), Seong, D C, Kantarjian, H M, Ro, J Y, Ralpaz, M, Xu, J. Robinson, J R, Deisseroth, A B, Champlin, R E, Siciliano, M J, *Blood* 86:2343 (1995).

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. A DNA probe set, said probe set comprising a first probe set and a second probe set, said first probe set being sufficient in length and substantially complementary to an entire breakpoint region of a first DNA and nucleotides on both sides of the breakpoint region but less than an entire chromosome such that said first probe set will hybridize to both sides of the breakpoint region regardless of whether the first DNA has been broken in the breakpoint region and either end fused to another DNA, and said second probe set being sufficient in length and substantially complementary to an entire breakpoint region of a second DNA and nucleotides on both sides of the breakpoint region but less than an entire chromosome such that said second probe set will hybridize to both sides of the breakpoint region regardless of whether the second DNA has been broken in the breakpoint region and either end fused to another DNA.

2. The probe set of claim 1, wherein said probes are detectably labelled.

3. The probe set of claim 2, wherein said first DNA is part of the ABL1 gene on chromosome 9 and the second DNA is part of the BCR gene on chromosome 22.

4. The probe set of claim 2, wherein said first DNA is part of the AML1 gene on chromosome 21 and the second DNA is part of the ETO gene on chromosome 8.

5. A diagnostic kit for detecting a structural abnormality caused by chromosomal breakage and rearrangement containing a reagent comprising at least one probe set of the probe set according to claim 1, and a container containing said reagent.

6. A diagnostic kit according to claim 5 further comprising at least two containers, wherein a first container contains a reagent comprising said first probe set and a second container contains a reagent comprising said second probe set.

7. A diagnostic kit according to claim 6 wherein said reagent comprises said first and said second probe set.

8. A DNA probe set, said probe set comprising a first probe set and a second probe set, said first probe set being sufficient in length and substantially complementary to an entire breakpoint region of a first DNA and nucleotides on both sides of the breakpoint region but less than an entire chromosome such that said first probe set will hybridize to both sides of the breakpoint region regardless of whether a second DNA from a region other than the breakpoint region has been inserted in the breakpoint region, and said second probe set being sufficient in length and substantially complementary to a 3' end and a 5' end of a second DNA but less than an entire chromosome such that said second probe set will hybridize to both ends of the second DNA regardless of whether the second DNA is inserted in the first DNA.

9. The probe set of claim 8, wherein said probes are detectably labelled.

10. A DNA probe set, said probe set comprising a first probe set and a second probe set, said first probe set being sufficient in length and substantially complementary to nucleotides on both sides of the breakpoint region of a first DNA but less than an entire chromosome such that said first probe set will hybridize to both sides of the breakpoint region regardless of whether the first DNA has been broken in the breakpoint region and either end fused to another DNA, and said second probe set being sufficient in length and substantially complementary to nucleotides on both sides of the breakpoint region of a second DNA but less than an entire chromosome such that said second probe set will hybridize to both sides of the breakpoint region regardless of whether the second DNA has been broken in the breakpoint region and either end fused to another DNA.

11. The probe set of claim 10, wherein said probes are detectably labeled.

12. The probe set of claim 11, wherein said first DNA is part of the ABL1 gene on chromosome 9 and the second DNA is part of the BCR gene on chromosome 22.

13. The probe set of claim 11, wherein said first DNA is part of the AML1 gene on chromosome 21 and the second DNA is part of the ETO gene on chromosome 8.

14. A diagnostic kit for detecting a structural abnormality caused by chromosomal breakage and rearrangement containing a reagent comprising at least one probe set of the probe set according to claim 10, and a container containing said reagent.

15. A diagnostic kit according to claim 14 further comprising at least two containers, wherein a first container contains a reagent comprising said first probe set and a second container contains a reagent comprising said second probe set.

16. A diagnostic kit according to claim 15 wherein said reagent comprises said first and said second probe sets.

17. A diagnostic kit for detecting a structural abnormality caused by chromosomal breakage and rearrangement containing a reagent comprising at least one probe set of the probe set according to claim 8, and a container containing said reagent.

18. A diagnostic kit according to claim 17 further comprising at least two containers, wherein a first container contains a reagent comprising said first probe set and a second container contains a reagent comprising said second probe set.

19. A diagnostic kit according to claim 18 wherein said reagent comprises said first and said second probe sets.

* * * * *

UNITED STATES PATENT AND TRADEMARK OFFICE
CERTIFICATE OF CORRECTION

PATENT NO.    : 6,414,133 B1
DATED         : July 2, 2002
INVENTOR(S)   : Jeanne Dietz-Band et al.

It is certified that error appears in the above-identified patent and that said Letters Patent is hereby corrected as shown below:

<u>Drawings,</u>
Figure 3, insert the sheet labeled "FIG. 3 Continued" which begins with the graph titled PT.4 immediately behind the first sheet of Figure 3, as shown on attached page.
Figure 3, insert the sheet labeled "FIG. 3 Continued" which begins with the graph titled PT.7 immediately behind the sheet labeled "FIG. 3 Continued" begins with the graph titled PT.4 as shown on attached page.
Figure 3, insert the sheet labeled "FIG. 3 Continued" which contains the graph titled PT.10 immediately behind the sheet labeled FIG. 3 Continued" which begins with the graph titled PT.7, as shown on attached page.

Signed and Sealed this

Twenty-ninth Day of July, 2003

JAMES E. ROGAN
*Director of the United States Patent and Trademark Office*

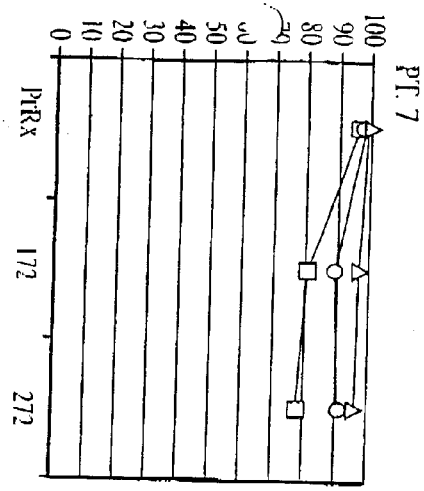
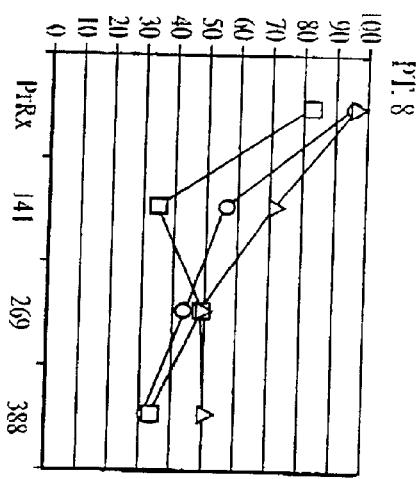
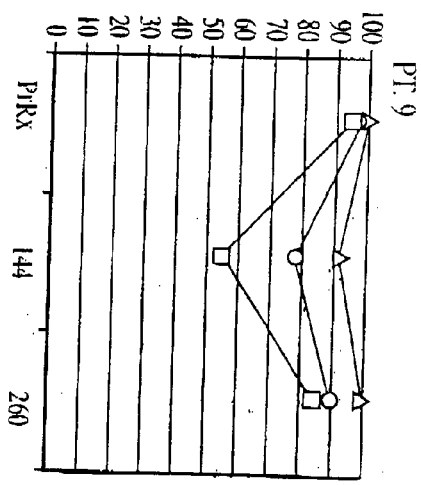
FIG. 3 CONTINUED

Adverse Decision In Interference

Patent No. 6,414,133, Jeanne Dietz-Band, Wang-Ting Hsieh, John F. Connaugton, MULTIPLE FUSION PROBES, Interference No. 105,208, final judgment adverse to the patentees rendered December 22, 2004, as to claims 1-3, 5-12, 14-19.

*(Official Gazette February 22, 2005)*

(12) EX PARTE REEXAMINATION CERTIFICATE (6766th)
United States Patent
Dietz-Band et al.

(10) Number: US 6,414,133 C1
(45) Certificate Issued: Apr. 14, 2009

(54) MULTIPLE FUSION PROBES

(75) Inventors: Jeanne Dietz-Band, Keedysville, MD (US); Wang-Ting Hsieh, Bethesda, MD (US); John F. Connaughton, Laytonsville, MD (US)

(73) Assignee: Ventana Medical Systems, Inc., Tucson, AZ (US)

Reexamination Request:
No. 90/007,000, Apr. 7, 2004

Reexamination Certificate for:
Patent No.: 6,414,133
Issued: Jul. 2, 2002
Appl. No.: 09/170,630
Filed: Oct. 13, 1998

Certificate of Correction issued Jul. 29, 2003.

(51) Int. Cl.
*C07H 21/04* (2006.01)
*C12P 19/34* (2006.01)
*C12Q 1/68* (2006.01)

(52) U.S. Cl. .................... 536/24.3; 536/23.1; 536/24.31; 536/24.32; 536/24.33; 435/6; 435/91.1

(58) Field of Classification Search ................. None
See application file for complete search history.

(56) References Cited

U.S. PATENT DOCUMENTS

| 5,447,841 | A |   | 9/1995 | Gray et al. |
|---|---|---|---|---|
| 5,721,098 | A | * | 2/1998 | Pinkel et al. ............ 435/6 |
| 6,025,126 | A |   | 2/2000 | Westbrook |
| 6,280,929 | B1 |   | 8/2001 | Gray et al. |
| 7,250,254 | B2 |   | 7/2007 | Dietz-Band et al. |
| 2004/0096872 | A1 |   | 5/2004 | Gray et al. |

FOREIGN PATENT DOCUMENTS

EP          0 430 402        1/1999

OTHER PUBLICATIONS

Elsas, F. J., "Comparison of direct and indirect fluorescent antibody methods for staining of Treponema pallidum," Brt. J. vener. Dis. 47: 255–258, 1971.*
Tkachuk et al., Detection of bcr/abl Fusion in Chronic Myelogenous Leukemia by in Situ Hybridization, Science, vol. 250, pp. 559–562, Oct. 26, 1990.*
New England BioLabs 1986/'87 Catalog, p. 64.*
Cassel et al., "Carrier–Specific Breakpoint–Spanning DNA Probes: an Approach to Preimplantation Genetic Diagnosis in Interphase Cells," *Human Reproduction* 12: 2019–2027 (Sep. 1997).
Arnoldus, E.P., et al., "Detection of the Philadelphia chromosome in interphase nuclei," *Cytogenet. Cell Genet.* 54:108–111, Basel Karger (1990).
Bartram, C.R., et al., "Translocation of c–ab1 oncogene correlates with the presence of a Philadelphia chromosome in chronic myelocytic leukaemia," *Nature* 306:277–280, Nature Publishing Group (1983).
Cassel, J.M., et al., "Carrier–specific breakpoint–spanning DNA probes: an approach to preimplantation genetic diagnosis in interphase cells," *Hum Reprod.* 12:2019–2027, Oxford University Press (1997).
Chan, L.C., et al., "A novel abl protein expressed in Philadelphia chromosome positive acute lymphoblastic leukaemia," *Nature* 325:635–637, Nature Publishing Group (1987).
Clark, S.S., et al., "Expression of a Distinctive BCR–ABL Oncogene in Ph1–Positive Acute Lymphocytic Leukemia (ALL)," *Science* 239:775–777, American Association for the Advancement of Science (1988).
de Klein, A., et al., "A cellular oncongene is translocated to the Philadelphia chromosome in chronic myelocytic leukaemia," *Nature* 300:765–767, Nature Publishing Group (1982).
Erickson, P., et al., "Identification of Breakpoints in t(8;21) Acute Myelogenous Leukemia and Isolation of a Fusion Transcript, AML1/ETO, with Similarity to Drosophila Segmentation Gent, runt," *Blood* 80:1825–1831, American Society of Hematology (1992).
Fainstein, E., et al., "A new fused transcript in Philadelphia chromosome positive acute lymphocytic leukaemia," *Nature* 330:386–388, Nature Publishing Group (1987).
Groffen, J., et al., "Philadelphia Chromosomal Breakpoints Are Clustered within a Limited Region, bcr, on Chromosome 22," *Cell* 36:93–99, Cell Press (1984).
Grosveld, G., et al., "The Chronic Myelocytic Cell Line K562 Contains a Breakpoint in bcr and Produces a Chimeric bcrlc–abl transcript," *Mol. Cell. Biol.* 6:607–616, American Society for Microbiology (1986).
Heisterkamp, N., et al., "Localization of the c–abl oncogene adjacent to a translocation break point in chronic myelocytic leukaemia," *Nature* 306:239–242, Nature Publishing Group (1983).
Heisterkamp, N., et al., "Structural organization of the bcr gene and its role in the Ph' translocation," *Nature* 315:758–761, Nature Publishing Group (1985).
Heisterkamp, N., et al., "The Human v–abl Cellular Homologue," *J. Mol. Appl. Genet.* 2:57–68, Raven Press (1983).

(Continued)

*Primary Examiner*—Gary L Kunz

(57) ABSTRACT

The invention is directed to a DNA probe set, the probe set comprising a first probe set and a second probe set, the first probe set being sufficient in length and substantially complementary to an entire breakpoint region of a first DNA and nucleotides breakpoint region but less than an entire chromosome such that the first probe set will hybridize to both sides of the breakpoint region regardless of whether the first DNA has been broken in the breakpoint region and either end fused to another DNA, and the second probe set being sufficient in length and substantially complementary to an entire breakpoint region of a second DNA and nucleotides on both sides of the breakpoint region but less than an entire chromosome such that the second probe set will hybridize to both sides of the breakpoint region regardless of whether the second DNA has been broken in the breakpoint region and either end fused to another DNA. Diagnostic kits utilizing the probe sets of the invention are also claimed.

OTHER PUBLICATIONS

Heisterkamp, N., et al., "The first BCR gene intron contains breakpoints in Philadelphia chromosome positive leukemia," *Nucleic Acids Res.* 16:10069–10081, IRL Press (1988).

Hermans, A., et al., "Unique Fusion of bcr and c–abl Genes in Philadelphia Chromosome Positive Acute Lymphoblastic Leukemia," *Cell* 51:33–40, Cell Press (1987).

Kawasaki, E.S., et al., "Diagnosis of chronic myeloid and acute lymphocytic leukemias by detection of leukemia–specific mRNA sequences amplified in vitro," *Proc. Natl. Acad. Sci. USA* 85:5698–5702, National Academy of Sciences (1988).

Kearney, L., et al., "DNA Sequences of Chromosome 21–Specific YAC Detect the t(8;21) Breakpoint of Acute Myelogenous Leukemia," *Cancer Genet. Cytogenet.* 57:109–119, Elsevier Science (1991).

Lichter, P., et al., "Rapid detection of human chromosome 21 aberrations by in situ hybridization," *Proc. Natl. Acad. Sci. USA* 85:9664–9668, National Academy of Sciences (1988).

Nisson, P.E., et al., "Transcriptionally Active Chimeric Gene Derive from the Fusion of the AML 1 Gene and a Novel Gene on the Chromosome 8 in t(8;21) Leukemic Cells," *Cancer Genet. Cytogenet.* 63:81–88, Elsevier Science (1992).

Ohyashiki, K., et al., "Philadelphia Chromosome–Positive Chronic Myelogenous Leukemia with Deleted Fusion of BCR and ABL Genes," *Jpn. J. Cancer Res.* 81:35–42, Japanese Cancer Association (1990).

Pinkel, D., et al., "Fluorescence in situ hybridization with human chromosome–specific libraries: Detection of trisomy 21 and translocations of chromosome 4," *Proc. Natl. Acad. Sci. USA* 85:9138–9142, National Academy of Sciences (1988).

Saachi, N., et al., "Interphase Cytogenetics of the t(8;21)(q22;q22) Associated with Acute Myelogenous Leukemia by Two–Color Fluorescence In Situ Hybridization," *Cancer Genet. Cytogenet.* 79:97–103, Elsevier Science (1995).

Shtalrid, M., et al., Analysis of Breakpoints within the bcr Gene and their Correlation with the Clinical Course of Philadelphia–Positive Chronic Myelogenous Leukemia, *Blood* 72:485–490, American Society of Hematology (1988).

Shtivelman, E., et al., "Alternative Splicing of RNAs Transcribed from the Human abl Gene and from the bcr–abl Fused Gene," *Cell* 47:277–284, Cell Press (1986).

Tkachuk, D.C., et al., "Detection of bcr–abl Fusion in Chronic Myelogeneous Leukemia by in Situ Hybridization," *Science* 250:559–562, American Association for the Advancement of Science (1990).

Westbrook, C.A., et al., "Long–Range Mapping of the Philadelphia Chromosome by Pulsed–Field Gel Electrophoresis," *Blood* 71:697–702, Grune and Stratton, Inc. (1988).

Bernards, A., et al., "The First Intron in the Human c–abl Gene Is at Least 200 Kilobases Long and Is a Target for Translocations in Chronic Myelogenous Leukemia," *Molec. Cell. Biol.* 7:3231–3236, American Society for Microbiology (1987).

Cleary, M.L., et al., "Chromosomal Translocation Involving the β T Cell Receptor Gene in Acute Leukemia," *J. Exp. Med.* 167:682–687, The Rockefeller University Press (1988).

Dalla Favera, R., et al., "Cloning and Characterization of Different Human Sequences Related to the onc gene (v–myc) of Avian Myelocytomatosis Virus (MC29)," *Proc. Natl. Acad. Sci. USA* 79:6497–6501, National Academy of Sciences (1982).

Declaration of A. Thomas Look, M.D. and Curriculum Vitae of A. Thomas Look, M.D., Patent Interference No. 105,208, *Dietz–Band v. Gray*, Gray Exhibits 1001 and 1002, respectively (Sep. 2004).

Dietz–Band Declaration of Janet D. Rowley, M.D. and Curriculum Vitae of Janet D. Rowley, M.D., Patent Interference No. 105,208, *Dietz–Band v. Gray*, Dietz–Band Exhibits 2014 and 2015, respectively (Jul. 2004).

Gauwerky, C.E., et al., "Evolution of B–cell Malignancy: Pre–B–cell Leukemia Resulting from MYC Activation in a B–cell Neoplasm with a Rearranged BCL2 gene," *Proc. Natl. Acad. Sci. USA* 85:8548–8552, National Academy of Sciences (1988).

Mellentin, J.D., et al., "lyl–1, a Novel Gene Altered by Chromosomal Translocation in T Cell Leukemia, Codes for a Protein with a Helix–Loop–Helix DNA Binding Motif," *Cell* 58:77–83, Cell Press (1989).

Mellentin, J.D., et al., "The Gene for Enhancer Binding Proteins E12/E47 Lies at the t(1;19) Breakpoint in Acute Leukemias," *Science* 246:379–382, American Association for the Advancement of Science (1989).

Ohno, H., et al., "Molecular Analysis of a Chromosomal Translocation, t(9;14)(p13;q32), in a Diffuse Large–cell Lymphoma Cell Line Expressing the Ki–1 Antigen," *Proc. Natl. Acad. Sci. USA* 87:628–632, National Academy of Sciences (1990).

Showe, L.C., et al., "Cloning and Sequencing of a c–myc Oncogene in a Burkitt's Lymphoma Cell Line That Is Translocated to a Germ Line Alpha Switch Region," *Molec. Cell. Biol.* 5:501–509, American Society for Microbiology (1985).

Zutter, M., et al., "The t(10;14)(q24;q11) of T–cell Acute Lymphoblastic Leukemia Juxtaposes the δ T–cell Receptor with TCL3, a Conserved and Activated Locus at 10q24," *Proc. Natl. Acad. Sci. USA* 87:3616–3615, National Academy of Sciences (1990).

Chase, A. et al., "Factors Influencing the False Positive and Negative Rates of BCR–ABL Fluorescence In Situ Hybridization," *Genes, Chromosomes & Cancer* 18:246–253, Wiley–Liss, Inc. (Apr. 1997).

Dewald, G.W. et al., "The application of Fluorescent In Situ Hybridization to Detect Mbcr/abl Fusion in Varian Ph Chromosomes in CML and ALL," *Cancer Genetics and Cytogenetics* 71:7–14, Elsevier Scientific Publishing Co., Inc. (1993).

Mühlmann J.et al., "Fluorescence In Situ Hybridization (FISH) on Peripheral Blood Smears for Monitoring Philadelphia Chromosome–Positive Chronic Myeloid Leukemia (CML) During Interferon Treatment: A New Strategy for Remission Assessment," *Genes, Chromosomes & Cancer* 21:90–100, Wiley–Liss, Inc. (Feb. 1996).

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–19 are cancelled.

New claims 20–29 are added and determined to be patentable.

*20. A DNA probe set that can detect at least two fusion events in a biological sample containing a chromosomal translocation, said probe set comprising a first probe set and a second probe set,*

*said first probe set being directly detectably labeled with a fluorophore and sufficient in length and substantially complementary to an entire breakpoint region of a first DNA and nucleotides on both sides of the breakpoint region beyond the 3' and 5' ends of the breakpoint region but less than an entire chromosome, such that said first probe set will hybridize to both sides of the breakpoint region regardless of whether said translocation has occurred, and*

*said second probe set being directly detectably labeled with a fluorophore different from that in said first probe set and sufficient in length and substantially complementary to an entire breakpoint region of a second DNA and nucleotides on both sides of the breakpoint region beyond the 3' and 5' ends of the breakpoint region but less than an entire chromosome, such that said second probe set will hybridize to both sides of the breakpoint region regardless of whether said translocation has occurred,*

*wherein said first DNA and said second DNA are from different non-homologous chromosomes,*

*wherein, if said translocation is present in said biological sample, said DNA probe set typically produces at least two fusion signals as well as two normal signals following hybridization to said first DNA and said second DNA,*

*wherein said at least two fusion signals and said two normal signals are detectable due to said different detectable fluorophore labels on said first probe set and said second probe set; and*

*wherein said DNA probe set does not comprise an entire genome.*

*21. The DNA probe set of claim 20 wherein said fluorophores are selected from the group consisting of FITC, Rhodamine and Texas Red.*

*22. The DNA probe set of claim 20, wherein said first DNA is part of the ABL1 gene on chromosome 9 and the second DNA is part of the BCR gene on chromosome 22.*

*23. The DNA probe set of claim 20, wherein said first DNA is part of the AML1 gene on chromosome 21 and the second DNA is part of the ETO gene on chromosome 8.*

*24. A diagnostic kit for detecting a reciprocal translocation comprising said first probe set and said second probe set of claim 20, in at least one container.*

*25. The diagnostic kit of claim 24, wherein said first probe set is in one container and said second probe set is in a second container.*

*26. A diagnostic kit for detecting a reciprocal translocation comprising said first probe set and said second probe set of claim 22, in at least one container.*

*27. The diagnostic kit of claim 26, wherein said first probe set is in one container and said second probe set is in a second container.*

*28. A diagnostic kit for detecting a reciprocal translocation comprising said first probe set and said second probe set of claim 23, in at least one container.*

*29. The diagnostic kit of claim 28, wherein said first probe set is in one container and said second probe set is in a second container.*

\* \* \* \* \*